US006093568A

United States Patent [19]
Davies et al.

[11] Patent Number: 6,093,568
[45] Date of Patent: *Jul. 25, 2000

[54] PLANT LYSOPHOSPHATIDIC ACID ACYLTRANSFERASES

[75] Inventors: Huw Maelor Davies; Deborah Hawkins; Janet Nelsen, all of Davis, Calif.

[73] Assignee: Calgene, Inc., Davis, Calif.

[ * ] Notice: This patent is subject to a terminal disclaimer.

[21] Appl. No.: 08/231,196

[22] Filed: Apr. 21, 1994

Related U.S. Application Data

[63] Continuation-in-part of application No. 08/224,625, Apr. 6, 1994, Pat. No. 5,563,058.

[51] Int. Cl.⁷ ............................. C12N 15/54; C12N 9/10; C12N 5/10; C12N 15/63

[52] U.S. Cl. ....................... 435/419; 435/172.3; 435/193; 435/252.3; 435/320.1; 435/325; 435/91.2; 536/23.1; 536/23.2; 536/23.6; 536/24.3; 536/24.1; 536/24.33

[58] Field of Search .................................. 536/23.1, 23.2, 536/23.6, 24.3, 24.1, 24.33; 435/172.3, 193, 240.2, 240.4, 252.3, 320.1, 91.2, 325, 419

[56] References Cited

FOREIGN PATENT DOCUMENTS

92/20236 11/1992 WIPO .

OTHER PUBLICATIONS

Bafor, et. al., "Substrate Specificities of Glycerol Acylating Enzymes from Developing Embryos of Two Cuphea Species", *Physiochemistry* 1992 vol. 31, No. 9 2973–2976 *08/224,625.

Bafor, et. al., "Regulation of Triacylglycerol Biosynthesis in Embryos and Microsomal Preparations from the Developing Seeds of *Cuphea lanceolata*" *Biochem J.* 1990 vol. 272 31–38 *08/224,625.

Bafor, et. al., Properties of Glycerol Acylating Enzymes in Microsomal Preparations from the Developing Seeds of Safflower (*Carthamus tinctorius*) and Turnip Rape (*Brassica campestris*) and their Ability to Assemble Cocoa–Butter Type Fats *JAOCS* 1990 vol. 67, No. 4 217–225 *08/224,625.

Bernerth, et. al., "Utilization of Erucoyl–CoA by Acyltransferases from Developing Seeds of *Brassica napus* (L.) Involved in Triacylglycerol Biosynthesis" *Plant Science* 1990 vol. 67 21–28 *08/224,625.

Cao, et. al., "Lysophosphatidate Acyltransferase in the Microsomes from Maturing Seeds of Meadowfoam (*Limnanthes alba*)" *Plant Physiol.* 1990 vol. 94 1199–1208 *08/224,625.

Coleman, J., "Characterization of the *Escherichia coli* Gene for 1–acyl–sn–glycerol–3–phosphate Acyltransferase (plsC)", *Mol. Gen. Genet.* 1992 vol. 232 295–303 *08/224,625.

Edwards, et. al., "Partial Purification and Properties of A Microsomal Lysophosphatidic Acid Acyltransferase from Oilseed Rape", *Biochemical Society Transactions* 1989 vol. 17 684–685 *08/224,625.

Frentzen, et. al., "Specificaties and Selectivities of Glycerol–3 Phosphate Acyltransferase and Monoacylglycerol–3–Phosphate Acyltransferase from Pea and Spinach Chloroplasts", *Eur. J. Biochem* 1983 vol. 129 629–636 *08/224,625.

Frentzen, et. al., "Intraorganelle Localization and Substrate Specificities of the Mitochondrial Acyl–CoA: sn–Glycerol–3–Phosphate O–Acyltransferases and Acyl–CoA: 1–Acyl–sn–Glycerol–3–Phosphate O–Acyltransferase from Potato Tubers and Pea Leaves" *Eur. J. Biochem* 1990 vol. 187 395–402 *08/224,625.

Hares, et. al., "Substrate Specificities of the Membrane–Bound and Partially Purified Microsomal Acyl–CoA:1–Acylglycerol–3–Phosphate Acyltransferase from Etiolated Shoots of *Pisum satavium* (L.)" *Planta 1991* vol. 185 124–131 *08/224,625.

Hares, et. al., "Properties of the Microsomal Acyl–CoA: sn–1–Acyl–Glycerol–3–Phosphate Acyltransferase from Spinach (*Spinacia oleracea* L.) Leaves" *J. Plant Physiol* 1987 vol. 131 49–59 *08/224,625.

Ichihara, et. al., "1–Acyl–sn–Glycerol–3–Phosphate Acyltransferase in Maturing Safflower Seeds and its Contributions to the Non–Random Fatty Acid Distribution of Triacylglycerol" *Eur. J. Biochem* 1987, vol. 167 339–347 *08/224,625.

Laurent, et. al. "Organ– and Development–Specific Acyl Coenzyme A Lysophosphatidate Acyltransferase in Palm and Meadowfoam" *Plant Physiol.* 1992 vol. 99 1711–1715 *08/224,625.

Nagiec, et. al. "A Suppressor Gene that Enables *Saccharomyces cerevisiae* to Grow without Making Sphingolipids Encodes a Protein that Resembles an *Escherichia coli* Fatty Acyltransferase" *The Journal of Biological Chemistry 1993*, vol. 268 No. 29 22156–22163 *08/224,625.

Oo, et. al. "Lysophosphatidate Acyltransferase Activities in the Microsomes from Palm Endosperm, Maize Scutellum, and Rapeseed Cotyledon of Maturing Seeds" *Plant Physiol. 1989*, vol. 91 1288–1295 *08/224,625.

Rajasekharan, et. al., "A Direct Nonchromatographic Assay for 1–Acyl–sn–Glycerol–3–Phosphate Acyltransferases" *Analytical Biochemistry* 1988, vol. 173 376–382 *08/224, 625.

(List continued on next page.)

*Primary Examiner*—Rebecca E. Prouty

[57] ABSTRACT

This invention relates to plant LPAATs, means to identify such proteins, amino acid and nucleic acid sequences associated with such protein, and methods to obtain, make and/or use such plant LPAATs. Purification, especially the removal of plant membranes and the substantial separation away from other plant proteins, and use of the plant LPAAT is provided, including the use of the protein as a tool in gene isolation for biotechnological applications. In addition, nucleic acid sequences encoding LPAAT protein regions are provided, and uses of such sequences for isolation of LPAAT genes from plants are considered.

26 Claims, 12 Drawing Sheets

OTHER PUBLICATIONS

Slabas, et. al. "Plastid and Cytoplasmic Synthesis of Lipids" *Biochemistry and Molecular Biology of Membrane and Storage Lipids of Plants*, Edited by Norio Murata, Chris Somerville, Proceedings US/Japan Binational Seminar, Kona, Hawaii Dec. 13–17, 1992 113–120 Enclosed.

Slabas, et. al. "Fatty Acid Synthesis in Oilseeds" Proceedings of the Phytochemical Society of Europe Chapter 5, "Seed Storage Compounds" Edited by Shewry, Peter and Stobart, Keith Clarendon Press 1993, 87–95 *08/224,625.

Sun, et. al. "Acyl Coenzyme A Preference of the Glycerol Phosphate Pathway in the Microsomes from the Maturing Seeds of Palm, Maize and Rapeseed" *Plant Physiol. 1988* vol. 88 56–60 *08/224,625.

Taylor, et. al., "Biosynthesis of Triacylglycerols in Brassica napus L. cv. Reston; Target: Trierucin" National Research Council of Canada No. 35122, Chapter 10 77–102 *08/224,625.

Wolter, et. al. "Biochemische und Molekularbiologische Ansatze zur Veranderung der Fettsaurezusammensetzung des Rapsols" *Fat. Sci. Technol. 1991* vol. 93 No. 8 288–290 *08/224,625.

S.J. Gould et al., "Use of the DNA Polymerase Chain Reaction for Homology Probing . . . ", Proc. Natl. Acad. Sci., 86: 1934–1938 (Mar. 1989).

B.G. Lyapkov et al., "Molecular Forms of Triacylglycerols From Edible Vegetable Oils", Prikl. Biokhim. Mikrobiol. 26(2) 157–167 (1990).

D.L. Cooper et al., "Full Length cDNA Cloning Utilizing the Polymerase Chain Reaction, a Degenerate Oligonucleotide Sequence and a Universal Primer", Biotechniques 9(1) 60–65, 1990.

M.A. Frohman et al., "Rapid Production of Full–Length cDNAs From Rare Transcripts: Amplification Using a Single Gene–Specific Oligonucleotide Primer", Proc. Natl. Acad. Sci. 85: 8998–9002, Dec. 1988.

N. Zilberberg et al., "Raid Isolation of Full Length cDNA Clones by Inverse PCR: Purification of a Scorpion cDNA Family Encoding Alpha–Neurotoxins", Anal. Biochem. 209: 203–205, 1993.

G. Peterek et al., "Heterologous Complementation For Cloning Genes Encoding Microsomal 1–Acylglycerol–3–Phosphate Acyltransferase", Biol. Chem. Hoppe–Seyler 374(8): 533, Aug. 1993.

A.P. Brown et al., "Identification of a cDNA That Encodes a 1–Acyl–sn–Glycerol–3–Phosphate Acyltransferase From Limnanthes douglasii", Plant Mol. Biol. 29: 267–278, 1995.

GenBank entry Z46846, 1994.

```
CTACTACTAC TA ATA ATA TTT CCG GAG GGG T ACT CGA TCG AAA ACA GGA      49
              Ile Ile Phe Pro Glu Gly   Thr Arg Ser Lys Thr Gly
                        SQ1256

AGG CTG CTT CCA TTT AAG AAG GGT TTT ATT CAC ATA GCA CTT CAG ACA      97
Arg Leu Leu Pro Phe Lys Lys Gly Phe Ile His Ile Ala Leu Gln Thr

CGG TTG CCG ATA GTT CCA ATG GTG CTG ACG GGT ACC CAT CTA GCT TGG     145
Arg Leu Pro Ile Val Pro Met Val Leu Thr Gly Thr His Leu Ala Trp
                                            SQ1271

AGG AAC AGT TTG CGA GTC AGA CCA GCA CCT ATC ACA GTG AAA             190
Arg Lys Asn Ser Leu Arg Val Arg Pro Ala Pro Ile Thr Val Lys
                  SQ1276 and SQ1282

TAC TTC TCA CCC ATA AAA ACT GAT GAC TGG GAA GAA GAA AAG ATC         235
Tyr Phe Ser Pro Ile Lys Thr Asp Asp Trp Glu Glu Glu Lys Ile
         SQ1262 and SQ1281

AAT CAT TAT GTG GAA ATG ATC CAC ATGATGATGA TG                       271
Asn His Tyr Val Glu Met Ile His
              SQ1272
```

FIGURE 10

```
CTACTACTAC TA ATA ATA TTC CCC GAA GGT ACT CGA TCG AAA ACA GGA AGG    51
           Ile Ile Phe Pro Glu Gly Thr Arg Ser Lys Thr Gly Arg
                   SQ1256

CTG CTT CCA TTT AAG AAG GTAACGATCA TAACATGCGT GTATATTTGT             99
Leu Leu Pro Phe Lys Lys

ATGTTTATCC ATTTTATTCT TCTGCTTGTG CTTCTCGTTT CTTCATTTTC TGTTGCAG     157

GGT TTT ATT CAC ATA GCA CCT CAG ACA CGG TTG CCG ATA GTT CCA ATG     205
Gly Phe Ile His Ile Ala Pro Gln Thr Arg Leu Pro Ile Val Pro Met

GTG CTG ACG GGT ACC CAT CTA GCT TGG AGG AAG AAC AGT TTG CGA GTC     253
Val Leu Thr Gly Thr His Leu Ala Trp Arg Lys Asn Ser Leu Arg Val
              SQ1271

AGA CCA GCA CCT ATC ACA GTG AAA TAC TTC TCA CCC ATA AAA ACT GAT     301
Arg Pro Ala Pro Ile Thr Val Lys Tyr Phe Ser Pro Ile Lys Thr Asp
     SQ1276 and SQ1282              SQ1262 and SQ1281

GAC TGG GAA GAA AAG ATC AAT CAT TAT GTC GAA ATG ATT CAC             346
Asp Trp Glu Glu Lys Ile Asn His Tyr Val Glu Met Ile His
                                       SQ1272

ATGATGATGA TG                                                       358
```

FIGURE 11

```
TACTACTACT A ATA ATA TTT CCC GAG GGT ACT CGA TCG AAA ACA GGA AGG    50
            Ile Ile Phe Pro Glu Gly Thr Arg Ser Lys Thr Gly Arg
                                SQ1256

CTG CTT CCA TTT AAG AAG GGT TTT ATT CAC ATA GCA CTT CAG ACA CGG     98
Leu Leu Pro Phe Lys Lys Gly Phe Ile His Ile Ala Leu Gln Thr Arg

TTG CCG ATA GTT CCA ATG GTG CTG ACG GGT ACC CAT CTA GCT TGG AGG    146
Leu Pro Ile Val Pro Met Val Leu Thr Gly Thr His Leu Ala Trp Arg
                                          SQ1271

AAG AAC AGT TTG CGA GTC AGA CCA GCA CCT ATC ACA GTG AAA TAC TTT    194
Lys Asn Ser Leu Arg Val Arg Pro Ala Pro Ile Thr Val Lys Tyr Phe
                    SQ1276 and SQ1282

TCG CCG ATC AAA ATGATGATGA TG                                      218
Ser Pro Ile Lys
    SQ1262
```

FIGURE 12

PLANT LYSOPHOSPHATIDIC ACID ACYLTRANSFERASES

This application is a continuation-in-part of application Ser. No. 08/224,625 filed Apr. 6, 1994 now U.S. Pat. No. 5,563,058.

TECHNICAL FIELD

The present invention is directed to protein preparations, amino acid and nucleic acid sequences and constructs, and methods related thereto.

BACKGROUND

There is a need for improved means to obtain or manipulate fatty acid compositions, from biosynthetic or natural plant sources. For example, novel oil products, improved sources of synthetic triacylglycerols (triglycerides), alternative sources of commercial oils, such as tropical oils (i.e., palm kernel and coconut oils), and plant oils found in trace amounts from natural sources are desired for a variety of industrial and food uses.

To this end, the triacylglycerol (TAG) biosynthesis system in plants and bacteria has been studied. In the cytoplasmic membranes of plant seed tissues which accumulate storage triglycerides ("oil"), fatty acyl groups at the sn-2 position of the triglyceride molecules are incorporated via action of the enzyme 1-acylglycerol-3-phosphate acyltransferase (E.C. 2.3.1.51), also known as lysophosphatidic acid acyltransferase, or LPAAT.

By inspection of the LPAAT activities in isolated membranes from seed tissues, it has been shown that LPAAT specificities vary from species to species in accordance with the kinds of fatty acyl groups found in the sn-2 positions of the respective storage oils. For example, in the seeds of Cuphea species, which accumulate oils containing medium-chain fatty acids, it is possible to demonstrate an LPAAT activity which will utilize medium-chain acyl-CoA and lysophosphatidic acid (LPA) substrates. In contrast, LPAAT activity from the membranes of rapeseed embryos, in which the oil contains fatty acids of longer chain length, uses these medium-chain substrates much less readily, and predominantly uses long-chain unsaturated fatty acids. Similarly the meadowfoam plant (*Limnanthes alba*) accumulates an oil containing erucic acid (22:1) in all three sn positions and has a seed LPAAT activity able to use 22:1-CoA and 22:1-LPA, whereas rapeseed, which does not accumulate these fatty acids, has little or no such 22:1-utilizing LPAAT.

Similar studies with the enzymes responsible for the sn-1 and sn-3 acylations show that they are much less selective with respect to the substrate chain lengths. Thus, for a specific storage triglyceride in a given plant, the types of fatty acyl groups found in the sn-2 position of the oil are determined primarily by the specificity of LPAAT with respect to its acyl-donor substrates, i.e. acyl-CoAs. In addition, the selectivity of the LPAAT towards the acyl-CoAs is also influenced by the nature of the acyl group already attached in the sn-1 position of the acceptor substrates, i.e. the 1-acylglycerol-3-phosphate or lysophosphatidic acid (LPA) molecules.

The characterization of lysophosphatidic acid acyltransferase (also known as LPAAT) is useful for the further study of plant FAS systems and for the development of novel and/or alternative oils sources. Studies of plant mechanisms may provide means to further enhance, control, modify or otherwise alter the total fatty acyl composition of triglycerides and oils. Furthermore, the elucidation of the factor(s) critical to the natural production of triglycerides in plants is desired, including the purification of such factors and the characterization of element(s) and/or co-factors which enhance the efficiency of the system. Of special interest are the nucleic acid sequences of genes encoding proteins which may be useful for applications in genetic engineering.

LITERATURE

Published characterizations of acyltransferase specificities in rapeseed membranes report that acyl group discrimination occurs primarily at the sn-2 acylation (Oo et al., *Plant Physiol.* (1989) 91:1288–1295; Bernerth et al, *Plant Sci.* (1990) 67:21–28).

Coleman (*Mol. Gen. Genet.* (1992) 232:295–303) reports the characterization of an *E. coli* gene (plsc) encoding LPAAT. The *E. coli* LPAAT is capable of utilizing either acyl-CoA or acyl-ACP as the fatty acyl donor substrate.

Hares & Frentzen (*Planta* (1991) 185:124–131) report solubilization and partial purification of a long-chain preferring LPAAT from endoplasmic reticulum in pea shoots. The purported solubilization is based solely on the inability to sediment LPAAT activity by high-speed centrifugation.

Wolter et al. (*Fat Sci. Technol.* (1991) 93: 288–290) report failed attempts to purify a *Limnanthes douglasii* acyltransferase catalyzing the acylation of erucic acid to the sn-2 position of the glycerol backbone, and propose hypothetical methods of gene isolation based on cDNA expression in microorganisms.

Nagiec et al. (*J. Biol. Chem.* (1993) 268:22156–22163) report the cloning of an SLCI (sphingolipid compensation) gene from yeast and report homology of the encoded protein to the LPAAT protein of *E. coli*.

Taylor et al. (in "Seed Oils for the Future", ed. Mackenzie & Taylor (1992) AOCS Press) report acyl-specificities for 18:1-CoA and 22:1-CoA substrates for LPAATs from several plant species and discuss attempts to purify a *B. napus* LPAAT.

Slabas et al. (Ch. 5, pages 81–95 (1993) in *Seed Storage Compounds: Biosynthesis, Interactions, and Manipulation,* ed Shewry & Stobart, Clarendon Press) discuss attempts to purify plant LPAAT proteins and note that all attempts to purify LPAAT to homogeneity have failed. Attempts to clone a corn LPAAT gene by complementation of an *E. coli* mutation at plsC are also discussed Oo et al. (*Plant Physiol.* (1989) 91:1288–1295) report characterization of LPAAT specificities in membrane preparations of palm endosperm, maize scutellum, and rapeseed cotyledon.

Cao et al. (*Plant Physiol.* (1990) 94:1199–1206) report characterization of LPAAT activity in maturing seeds of meadowfoam, nasturtium, palm, castor, soybean, maize, and rapeseed. LPAAT activity was characterized with respect to 22:1 and 18:1 LPA and acyl-COA substrates.

Laurent and Huang (*Plant Physiol.* (1992) 99:1711–1715) report that LPAATs in palm and meadowfoam which are capable of transferring 12:0 and and 22:1 acyl-CoA substrates to the sn-2 position of LPA, are confined to the oil-accumulating seed tissues.

Bafor et al. (*Phytochemistry* (1990) 31:2973–2976) report substrate specificities of TAG biosynthesis enzymes, including LPAAT, from *Cuphea procumbens* and *C. wrighti*.

Bafor et al. (*Biochem. J.* (1990) 272:31–38) report results of studies on regulation of TAG biosynthesis in *Cuphea lanceolata* embryos. Results of assays for LPAAT activity in microsomal preparations from developing cotyledons are provided.

Frentzen et al. (*Eur. J. Biochem.* (1990) 187:389–402 report characterization of mitochondrial LPAAT activity in potato tubers and pea leaves.

BRIEF DESCRIPTION OF THE FIGURES

FIG. 10 provides DNA sequence and translated amino acid sequence of a clone, 23-2, containing LPAAT encoding sequence obtained by PCR.

FIG. 11 provides DNA sequence and translated amino acid sequence of a clone, 23-4, (SEQ ID NO:19) containing LPAAT encoding sequence obtained by PCR.

FIG. 12 provides DNA sequence and translated amino acid sequence of a clone, 10-1, (SEQ ID NO:2) containing LPAAT encoding sequence obtained by PCR.

SUMMARY OF THE INVENTION

Figure 1:
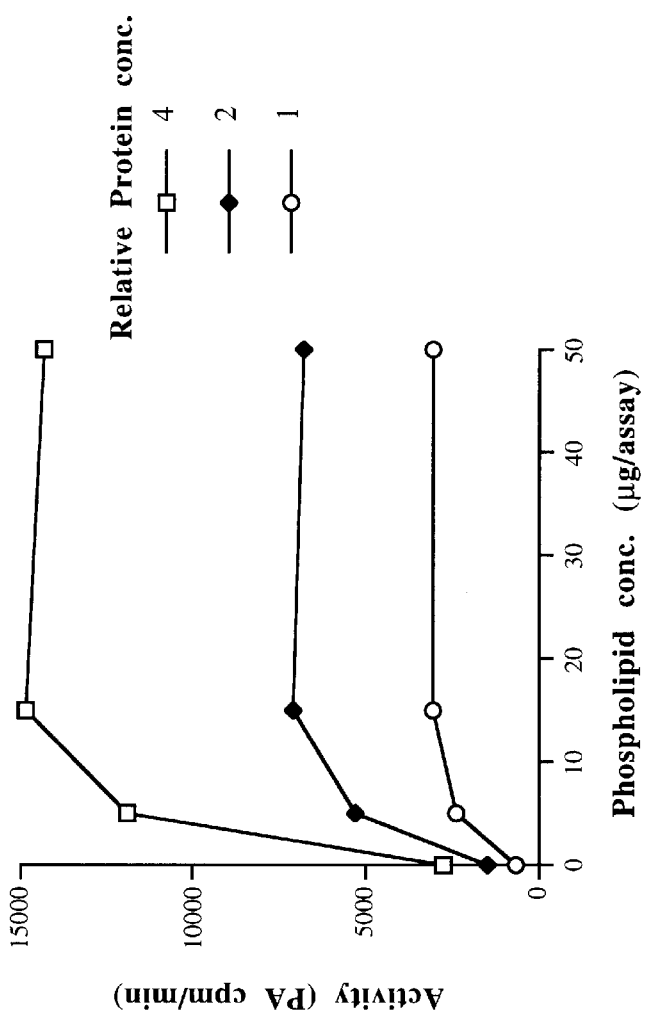
FIG. 1 shows the effect of soybean phospholipid concentration on coconut medium-chain LPAAT activity (assay of S3 preparation).

This invention relates to plant proteins which catalyze the production of 1,2-diacylglycerol-3-phosphate from 1-acylglycerol-3-phosphate (also referred to as lysophosphatidic acid or LPA) and an acyl-CoA substrate. Such proteins are referred to herein as 1-acylglycerol-3-phosphate acyltransferases (E.C. 2.3.1.51) or LPAATs. In particular, the LPAAT proteins of this invention demonstrate preferential activity on acyl-CoA donor substrates and little or no activity towards acyl-ACP donor substrates.

By this invention, plant LPAAT proteins are substantially purified away from the cytoplasmic membranes of their native plant host, and characterized with respect to preferential substrate activity. In particular, purification of a plant LPAAT enzyme having preferential activity towards medium-chain acyl-CoA substrates is provided.

A medium-chain preferring LPAAT of this invention demonstrates a preference for medium-chain acyl-CoA donor substrates, whether the LPA acceptor substrate contains a medium-chain acyl group (such as C12:0) at the sn-1 position or a long-chain acyl group (such as C18:1) at the sn-1 position. A coconut endosperm medium-chain acyl-CoA preferring LPAAT enzyme is exemplified herein. Lauroyl-CoA is a preferred donor substrate when the acceptor substrate is either 1-lauroylglycerol-3-phosphate or 1-oleoylglycerol-3-phosphate. In addition, the coconut LPAAT also demonstrates preferential activity on other medium-chain acyl-CoA substrates, particularly those having C10 or C14 carbon chains, as compared to longer chain length (C16 or C18) substrates.

The exemplified coconut LPAAT is purified away from the membranes (i.e. solubilized), and the solubilized LPAAT preparation is subjected to various chromatographic analyses to identify a protein associated with the LPAAT activity. In this manner a protein having a molecular weight of approximately 27–29 kDA is identified as associated with LPAAT activity. Further purification methods, such as column chromatography and polyacrylamide gel electrophoresis are utilized to obtain the LPAAT protein in sufficient purity for amino acid sequence analysis.

As a result, LPAAT peptide sequences are determined, and an LPAAT peptide fragment having sequence homology to a non-plant LPAAT (*E. coli* plsC gene product) is discovered. The LPAAT peptide sequences are used as templates in designing various synthetic oligonucleotides which are then used to obtain nucleic acid sequences encoding all or a portion of the coconut LPAAT protein.

LPAAT PCR product sequences are provided in the instant application and used to obtain cDNA clones encoding coconut LPAAT. Using the coconut LPAAT encoding sequences so obtained, it is also possible to isolate other plant LPAAT genes which encode LPAAT proteins of different specificities with respect to acyl-CoA donor substrates (e.g. 8:0, 10:0, 14:0, 22:1 etc.).

Thus, this invention encompasses plant LPAAT peptides and the corresponding amino acid sequences of those peptides, and the use of these peptide sequences in the preparation of oligonucleotides containing LPAAT encoding sequences for analysis and recovery of plant LPAAT gene sequences. The plant LPAAT encoding sequence may encode a complete or partial sequence depending upon the intended use. All or a portion of the genomic sequence, or cDNA sequence, is intended.

Of special interest are recombinant DNA constructs which provide for transcription or transcription and translation (expression) of the plant LPAAT sequences. In particular, constructs which are capable of transcription or transcription and translation in plant host cells are preferred. Such constructs may contain a variety of regulatory regions including transcriptional initiation regions obtained from genes preferentially expressed in plant seed tissue.

In yet a different aspect, this invention relates to a method for producing a plant LPAAT in a host cell or progeny thereof via the expression of a construct in the cell. Cells containing a plant LPAAT as a result of the production of the plant LPAAT encoding sequence are also contemplated herein.

In addition, this invention relates to methods of using DNA sequences encoding plant LPAAT for the modification of the proportion fatty acyl groups at the sn-2 position of the triglyceride molecules, especially in the seed oil of plant oilseed crops. Plant cells having such a modified triglyceride are also contemplated herein. Of particular interest is the use of a medium-chain preferring LPAAT sequence in Brassica plants which have been engineered to produce medium-chain fatty acids in the seed oil. In such plants, up to approximately 50 mol percent laurate is accumulated in the seed triglycerides. Most of this laurate, however, is esterified at the sn-1 and sn-3 positions due to the specificity of the Brassica LPAAT for longer chain length acyl-CoA substrates. By expression of a medium-chain preferring LPAAT protein in the seeds of such plants, it is possible to obtain Brassica seed oil which has greater than 67 mole percent laurate in the TAG.

Also considered in this invention are the modified plants, seeds and oils obtained by expression of the plant LPAAT proteins of this invention.

DETAILED DESCRIPTION OF THE INVENTION

A plant LPAAT of this invention includes any sequence of amino acids, such as a protein, polypeptide or peptide, obtainable from a plant source, which demonstrates the ability to catalyze the production of 1,2-diacylglycerol-3-phosphate from 1-acylglycerol-3-phosphate and an acyl-CoA substrate under plant enzyme reactive conditions. By "enzyme reactive conditions" is meant that any necessary conditions are available in an environment (i.e., such factors as temperature, pH, lack of inhibiting substances) which will permit the enzyme to function.

Preferential activity of a plant LPAAT toward particular chain-length fatty acyl-CoA substrates is determined upon comparison of 1,2-diacylglycerol-3-phosphate product amounts obtained per different chain length acyl-CoA donor substrates. In some cases, the chain length of an acyl group in the sn-1 position may also affect the ability of the LPAAT to utilize a given chain length acyl-CoA donor. Of particular interest in the instant invention is a medium-chain acyl-CoA preferring LPAAT in coconut immature endosperm tissue.

Medium-chain acyl-CoA preferring enzyme preparations include those which demonstrate a preference for medium-chain, i.e. C8, C10, C12 or C14 acyl-CoA donor substrates over acyl-CoA substrates of different acyl carbon lengths, regardless of the chain length of the acyl group in the sn-1 position of the acceptor LPA substrate. It is noted that some activity, of a lesser magnitude, may also be observed against other chain-length fatty acyl substrates, i.e., the specificity will be substantial, but may not be absolute. For example, the exemplified coconut LPAAT demonstrates a strong preference for C12 acyl-CoA donor substrates when the acceptor substrate is lauroyl-LPA, but also has significantly more activity towards C10 and C14 substrates as compared to longer chain substrates whose acyl groups have 16 or 18 carbons. When the acceptor substrate is 18:1-CoA, the coconut LPAAT uses C12 and C14 substrates at nearly equal rates, and still prefers these and C10 substrates over available long-chain acyl-CoA substrates.

Other plant LPAAT proteins may also demonstrate preferential activity on one or more medium-chain acyl-CoA substrates, but the preference may only be encountered where a medium-chain acyl group is present in the sn-1 position of the LPA donor substrate. Such LPAAT's are considered as having selective preference for medium-chain acyl-CoA substrates.

As noted above, a plant LPAAT of this invention will display activity toward fatty acyl-CoA substrates, and have little or no activity towards fatty acyl-ACP substrates. Thus, the LPAAT of the instant invention may be distinguished from plant chloroplastic LPAATs which demonstrate activity towards both acyl-ACP and acyl-CoA substrates.

The acyl-CoA LPAATs of the instant invention are present in cytoplasmic membranes in various plant tissues. Of particular interest are those LPAATs associated with the TAG biosynthesis pathway in the endoplasmic reticulum of immature seed tissues. Immature seed tissues containing such LPAATs may include embryo tissue or endosperm tissue, depending on the location of TAG biosynthesis in a particular plant species. In coconuts, for example, LPAAT activity is detected primarily in the endosperm tissue, the site of TAG biosynthesis. In California bay seeds, immature embryo cotyledons provide a good source of LPAAT activity, and in Brassica seeds, substantial LPAAT activity is also found in immature embryos.

The plant endoplasmic reticulum LPAAT enzymes studied to date have been found to be membrane proteins. Thus, in order to further study LPAAT activity, and in particular to produce purified preparations of such a protein by chromatographic methods, it is necessary to obtain the enzyme in solubilized form, i.e. separated from the cytoplasmic membrane environment.

"Solubilization" refers to extraction of the LPAAT enzyme from the membranes in such a way that it then behaves in a manner typical of enzymes that are not membrane-associated. Because the membrane effectively links the LPAAT protein to other proteins which are also present therein, solubilization is an essential requirement for identification and purification of the LPAAT protein as described in the following examples. In testing for solubilization of LPAAT activity, three different indications of solubilization, as described in more detail in the following examples, are considered.

1) LPAAT activity is not sedimented by very high-speed centrifugation.
2) LPAAT activity migrates on a size-exclusion chromatography column as though it had a native molecular weight typical of enzymes which are not membrane-associated.
3) Proteins present in the LPAAT preparation are at least partially separable from each other by column chromatography.

Because of potential alternative interpretations that may apply to any of the above criteria individually, it is necessary to confirm that all three of the criteria have been satisfied to confirm LPAAT solubilization. For example, the first criterion, of failure to sediment at very high g forces could be misleading if the density of the solution used for solubilization is similar to that of the unsolubilized membranes so that they sediment only very slowly. This situation is illustrated in the examples which follow, in which a published solubilization procedure that relied on this criterion alone, is shown to be inadequate to obtain LPAAT substantially separated from the cytoplasmic membranes. The second criterion, in which solubilized activity migrates more slowly through a size-exclusion column than the original membranes, may be compromised if the membranes themselves bind weakly to the column after exposure to detergent so that their migration through it is slowed. The third criterion, in which the solubilized proteins are chromatographically resolvable, is the least likely to be compromised by artifacts or unforeseen situations. However, it is possible that membranes could be partially dissociated by the solubilization procedure such that various aggregates of proteins are released. Such aggregates might then be resolved from each other chromatographically. Thus, satisfaction of all three criteria is necessary to assure that LPAAT solubilization is achieved.

Solubilization of coconut LPAAT in a solution containing 1M NaCl, 2.25% (w/v) CHAPS detergent, and a detergent/ protein ratio of 48/1 (w/w) is described in the following examples. Similarly, LPAAT activity from California bay is solubilized using a solubilization solution containing 1M NaCl, 4% (w/v) CHAPS detergent, and a detergent/protein ratio of 58/1 (w/w) Solubilization of the plant LPAATs is confirmed by demonstration of each of the above criteria of solubilization.

Furthermore, in studies of the solubilized LPAAT activity it was discovered, as described in detail in the following examples, that solubilized LPAAT could only be assayed by addition of concentrated phospholipids, to reconstitute LPAAT activity. In particular, the stimulatory action of phospholipds on LPAAT activity is greatest when the phospholipids are added to the solubilized LPAAT sample at the start of the assay procedure, followed by dilution of the high CHAPS and salt concentrations in this buffer by addition of the remaining assay ingredients. Addition of the phospholipids after dilution of the solubilization solution results in little or no increase in detection of LPAAT activity. The phospholipid stimulation effect is also seen where the phospholipids are added to a sample of solubilization buffer alone, followed by dilution with remaining assay ingredients and subsequent addition of the solubilized LPAAT sample.

Solubilized preparations of coconut endosperm LPAAT are utilized in a variety of chromatographic experiments for identification and partial purification of the LPAAT protein. In this manner, a protein having a molecular weight of approximately 27–29 kDa is identified as associated with LPAAT activity. As described in more detail in the following examples, the 29 kDa protein is partially purified by chromatography on red 120 agarose and hydroxyapatite columns. The protein is then obtained in substantially purified form by gel electrophoresis and blotting of the partially purified LPAAT preparation to nitrocellulose. The 27–29 kDA protein is recovered by cutting out that portion of the nitrocellulose filter containing the identified band.

The purified protein is then digested with various enzymes to generate peptides for use in determination of amino acid sequence. Amino acid sequence of a tryptic peptide obtained in this manner is demonstrated to share a region of homology with the LPAAT protein encoded by the $E.\ coli$ plsC gene. This same region shared by the $E.\ coli$ and coconut LPAATs is also found in a yeast acyltransferase protein encoded by the SLC1 gene.

Thus, the tryptic peptide of the 27–29 kDa protein described herein represents a portion of a medium chain-acyl-CoA preferring coconut LPAAT. Other coconut LPAAT peptides are similarly obtained and the amino acid sequences provided.

The use of amino acid sequences from LPAAT peptides to obtain nucleic acid sequences which encode coconut LPAAT is described herein. For example, synthetic oligonucleotides are prepared which correspond to the LPAAT peptide sequences. The oligonucleotides are used as primers in polymerase chain reaction (PCR) techniques to obtain partial DNA sequence of LPAAT genes. The partial sequences so obtained are then used as probes to obtain LPAAT clones from a gene library prepared from coconut tissue. Alternatively, where oligonucleotides of low degeneracy can be prepared from particular LPAAT peptides, such probes may be used directly to screen gene libraries for LPAAT gene sequences. In particular, screening of cDNA libraries in phage vectors is useful in such methods due to lower levels of background hybridization. DNA sequences of LPAAT peptide encoding sequences obtained in this manner are provided in the application.

A nucleic acid sequence of a plant LPAAT of this invention may be a DNA or RNA sequence, derived from genomic DNA, cDNA, mRNA, or may be synthesized in whole or in part. The gene sequences may be cloned, for example, by isolating genomic DNA from an appropriate source, and amplifying and cloning the sequence of interest using a polymerase chain reaction (PCR). Alternatively, the gene sequences may be synthesized, either completely or in part, especially where it is desirable to provide plant-preferred sequences. Thus, all or a portion of the desired structural gene (that portion of the gene which encodes the LPAAT protein) may be synthesized using codons preferred by a selected host. Host-preferred codons may be determined, for example, from the codons used most frequently in the proteins expressed in a desired host species.

One skilled in the art will readily recognize that antibody preparations, nucleic acid probes (DNA and RNA) and the like may be prepared and used to screen and recover "homologous" or "related" LPAATs from a variety of plant sources. Homologous sequences are found when there is an identity of sequence, which may be determined upon comparison of sequence information, nucleic acid or amino acid, or through hybridization reactions between a known LPAAT and a candidate source. Conservative changes, such as Glu/Asp, Val/Ile, Ser/Thr, Arg/Lys and Gln/Asn may also be considered in determining sequence homology. Amino acid sequences are considered homologous by as little as 25% sequence identity between the two complete mature proteins. (See generally, Doolittle, R. F., OF URFS and ORFS (University Science Books, CA, 1986.)

Thus, other plant LPAATs may be obtained from the specific exemplified coconut protein preparations and sequences provided herein. Furthermore, it will be apparent that one can obtain natural and synthetic plant LPAATs, including modified amino acid sequences and starting materials for synthetic-protein modeling from the exemplified plant LPAATs and from plant LPAATs which are obtained through the use of such exemplified sequences. Modified amino acid sequences include sequences which have been mutated, truncated, increased and the like, whether such sequences were partially or wholly synthesized. Sequences which are actually purified from plant preparations or are identical or encode identical proteins thereto, regardless of the method used to obtain the protein or sequence, are equally considered naturally derived.

Typically, a plant LPAAT sequence obtainable from the use of nucleic acid probes will show 60–70% sequence identity between the target LPAAT sequence and the encoding sequence used as a probe. However, lengthy sequences with as little as 50–60% sequence identity may also be obtained. The nucleic acid probes may be a lengthy fragment of the nucleic acid sequence, or may also be a shorter, oligonucleotide probe. When longer nucleic acid fragments are employed as probes (greater than about 100 bp), one may screen at lower stringencies in order to obtain sequences from the target sample which have 20–50% deviation (i.e., 50–80% sequence homology) from the sequences used as probe. Oligonucleotide probes can be considerably shorter than the entire nucleic acid sequence encoding an LPAAT enzyme, but should be at least about 10, preferably at least about 15, and more preferably at least about 20 nucleotides. A higher degree of sequence identity is desired when shorter regions are used as opposed to longer regions. It may thus be desirable to identify regions of highly conserved amino acid sequence to design oligonucleotide probes for detecting and recovering other related LPAAT genes. Shorter probes are often particularly useful for polymerase chain reactions (PCR), especially when highly conserved sequences can be identified. (See, Gould, et al., PNAS USA (1989) 86:1934–1938.)

In addition to isolation of other plant LPAATs, it is considered that genes for other related acyltransferase proteins may also be obtained using sequence information from the coconut LPAAT and related nucleic acid sequences. For example, other acyltransferase enzymes are involved in plant lipid biosynthesis, including plastidial LPAAT, mitochondrial LPAAT, lysophosphatidylcholine acyltransferase (LPCAT), lysophosphatidylserine acyltransferase (LPSAT), lysophosphatidylethanolamine acyltransferase (LPEAT), and lysophosphatidylinositol acyltransferase (LPIAT). These enzymes all catalyze acyltransferase reactions involving the sn-2 position of lysophospholipids, and the genes encoding these sequences may also be related to the plant acyl-CoA LPAAT sequences of the instant invention and obtainable therefrom.

To determine if a related gene may be isolated by hybridization with a given sequence, the sequence is labeled to allow detection, typically using radioactivity, although other methods are available. The labeled probe is added to a hybridization solution, and incubated with filters containing the desired nucleic acids, such as Northern or Southern blots, or the filters containing cDNA or genomic clones to be screened. Hybridization and washing conditions may be varied to optimize the hybridization of the probe to the sequences of interest. Lower temperatures and higher salt concentrations allow for hybridization of more distantly related sequences (low stringency). If background hybridization is a problem under low stringency conditions, the temperature can be raised either in the hybridization or washing steps and/or salt content lowered to improve detection of the specific hybridizing sequence. Hybridization and washing temperatures can be adjusted based on the estimated melting temperature of the probe as discussed in Beltz, et al. (*Methods in Enzymology* (1983) 100:266–285). A useful probe and appropriate hybridization and washing conditions having been identified as described above, CDNA or genomic libraries are screened using the labeled sequences and optimized conditions.

For immunological screening, antibodies to the coconut LPAAT protein can be prepared by injecting rabbits or mice with the purified protein, such methods of preparing antibodies being well known to those in the art. Either monoclonal or polyclonal antibodies can be produced, although typically polyclonal antibodies are more useful for gene isolation. Western analysis may be conducted to determine that a related protein is present in a crude extract of the desired plant species, as determined by cross-reaction with the antibodies to the coconut LPAAT. When cross-reactivity is observed, genes encoding the related proteins are isolated by screening expression libraries representing the desired plant species. Expression libraries can be constructed in a variety of commercially available vectors, including lambda gt11, as described in Maniatis, et al. (*Molecular Cloning: A Laboratory Manual*, Second Edition (1989) Cold Spring Harbor Laboratory, Cold Spring Harbor, N.Y.).

All plants utilize LPAAT proteins in production of membrane phospholipids, and thus any given plant species can be considered as a source of additional LPAAT proteins. Plants having significant medium-chain fatty acids in their seed oils are preferred candidates to obtain plant LPAATs capable of incorporating medium-chain fatty acids into the sn-2 position of TAG. Several species in the genus Cuphea accumulate triglycerides containing medium-chain fatty acids in their seeds, e.g., *procumbens, lutea, hookeriana, hyssopifolia, wrightii* and *inflata*. Another natural plant source of medium-chain fatty acids are seeds of the Lauraceae family. In addition to the exemplified California Bay (*Umbellularia californica*), Pisa (*Actinodophne hookeri*), Sweet Bay (*Laurus nobilis*) and *Cinnamomum camphora* (camphor) accumulate medium-chain fatty acids. Other plant sources include Ulmaceae (elm), Palmae, Myristicaceae, Simarubaceae, Vochysiaceae, and Salvadoraceae.

Also of particular interest are LPAATs from plant species which incorporate unusual long-chain fatty acids in the storage TAG. For example nasturtium and meadowfoam contain 22:1 acyl groups in the seed TAG, and meadowfoam has been shown to contain an LPAAT capable of incorporating 22:1 (erucic) fatty acyl groups into the sn-2 position. An LPAAT having such activity may find use in production of "tri-erucic" Brassica oil, which to date is not found due to the selectivity of Brassica seed LPAAT towards unsaturated fatty acids, such as 18:1 and 18:2.

In addition, LPAAT enzymes from plants which contain other unusual fatty acids are of interest and may find use for production of TAG containing these unusual fatty acids in various plant species. Of interest in this regard are LPAATs involved in the production of acetylenic fatty acids, such as crepenynic acid from *Crepis foetida;* fatty acids with cyclopentene substituents, such as gorlic acid from species of the family Flacourtiaceae; cyclopropane fatty acids, such as vernolic acid from *Vernonia galamensis;* hydroxylated fatty acids, such as ricinoleic acid from *Ricinus communis;* furan-containing fatty acids, such as from *Exocarpus cupressiformis;* fatty acids with several unusual functional groups, such as those from *Sapium sebiferum,* which contain multiple double bonds and an internal ester function; fatty acids with unusual double-bond placement, such as petroselinic acid from some species of Umbelliferae, Araliaceae, and Garryaceae; and medium-chain fatty acids containing double bonds, such as from Lindera species.

It should also be noted that plant LPAATs from a variety of sources can be used to investigate TAG biosynthesis events of plant lipid biosynthesis in a wide variety of in vivo applications. Because all plants appear to synthesize lipids via a common metabolic pathway, the study and/or application of one plant LPAAT to a heterologous plant host may be readily achieved in a variety of species. In other applications, a plant LPAAT can be used outside the native plant source of the LPAAT to enhance the production and/or modify the composition of the TAG produced or synthesized in vitro.

In addition, it is now found that LPAAT from *E. coli* and the coconut LPAAT have regions of conserved amino acid sequence, which regions are also conserved in a putative LPAAT protein from yeast. Thus, it may be possible to design probes from such conserved regions to isolate LPAAT encoding sequences from other organisms, such as from animals. Such LPAAT encoding sequences may also find use in applications described herein, in particular, in plant genetic engineering techniques for production of TAG having particular fatty acyl groups at the sn-2 position. For example, an animal LPAAT may find applications in plant genetic engineering to produce oils having long-chain saturated fatty acyl groups, such as 18:0 in the sn-2 position to provide a source of useful TAG for infant formula.

The nucleic acid sequences associated with plant LPAAT proteins will find many uses. For example, recombinant constructs can be prepared which can be used as probes, or which will provide for expression of the LPAAT protein in host cells to produce a ready source of the enzyme and/or to modify the composition of triglycerides found therein. Other useful applications may be found when the host cell is a plant host cell, either in vitro or in vivo. For example, by increasing the amount of a respective medium-chain preferring LPAAT available to the plant TAG biosynthesis pathway, an increased percentage of medium-chain fatty acids may be obtained in the TAG. In a like manner, for some applications it may be desired to decrease the amount of LPAAT endogenously expressed in a plant cell by antisense technology. For example, to allow for more opportunity for an inserted foreign LPAAT to transfer medium-chain or unusual longer-chain fatty acyl groups to the sn-2 position, decreased expression of a native Brassica long-chain preferring LPAAT may be desired.

Thus, depending upon the intended use, the constructs may contain the sequence which encodes the entire LPAAT protein, or a portion thereof. For example, where antisense inhibition of a given LPAAT protein is desired, the entire LPAAT sequence is not required. Furthermore, where LPAAT constructs are intended for use as probes, it may be advantageous to prepare constructs containing only a particular portion of an LPAAT encoding sequence, for example a sequence which is discovered to encode a highly conserved LPAAT region.

As discussed above, nucleic acid sequence encoding a plant LPAAT of this invention may include genomic, cDNA or mRNA sequence. By "encoding" is meant that the sequence corresponds to a particular amino acid sequence either in a sense or anti-sense orientation. By "extrachromosomal" is meant that the sequence is outside of the plant genome of which it is naturally associated. By "recombinant" is meant that the sequence contains a genetically engineered modification through manipulation via mutagenesis, restriction enzymes, and the like.

A cDNA sequence may or may not contain pre-processing sequences, such as transit peptide sequences or targetting sequences to facilitate delivery of the LPAAT protein (such as mitochondrial LPAAT) to a given organelle or membrane location. The use of any such precursor LPAAT DNA sequences is preferred for uses in plant cell expression. A genomic LPAAT sequence may contain the transcription and translation initiation regions, introns, and/or transcript termination regions of the plant LPAAT, which sequences may be used in a variety of DNA constructs, with or without the LPAAT structural gene. Thus, nucleic acid sequences corresponding to the plant LPAAT of this invention may also provide signal sequences useful to direct protein delivery into a particular organellar or membrane location, 5' upstream non-coding regulatory regions (promoters) having useful tissue and timing profiles, 3' downstream non-coding regulatory region useful as transcriptional and translational regulatory regions and may lend insight into other features of the gene.

Once the desired plant LPAAT nucleic acid sequence is obtained, it may be manipulated in a variety of ways. Where the sequence involves non-coding flanking regions, the flanking regions may be subjected to resection, mutagenesis, etc. Thus, transitions, transversions, deletions, and insertions may be performed on the naturally occurring sequence. In addition, all or part of the sequence may be synthesized. In the structural gene, one or more codons may be modified to provide for a modified amino acid sequence, or one or more codon mutations may be introduced to provide for a convenient restriction site or other purpose involved with construction or expression. The structural gene may be further modified by employing synthetic adapters, linkers to introduce one or more convenient restriction sites, or the like.

The nucleic acid or amino acid sequences encoding a plant LPAAT of this invention may be combined with other non-native, or "heterologous", sequences in a variety of ways. By "heterologous" sequences is meant any sequence which is not naturally found joined to the plant LPAAT, including, for example, combinations of nucleic acid sequences from the same plant which are not naturally found joined together.

The DNA sequence encoding a plant LPAAT of this invention may be employed in conjunction with all or part of the gene sequences normally associated with the LPAAT. In its component parts, a DNA sequence encoding LPAAT is combined in a DNA construct having, in the 5' to 3' direction of transcription, a transcription initiation control region capable of promoting transcription and translation in a host cell, the DNA sequence encoding plant LPAAT and a transcription and translation termination region.

Potential host cells include both prokaryotic and eukaryotic cells. A host cell may be unicellular or found in a multicellar differentiated or undifferentiated organism depending upon the intended use. Cells of this invention may be distinguished by having a plant LPAAT foreign to the wild-type cell present therein, for example, by having a recombinant nucleic acid construct encoding a plant LPAAT therein.

Depending upon the host, the regulatory regions will vary, including regions from viral, plasmid or chromosomal genes, or the like. For expression in prokaryotic or eukaryotic microorganisms, particularly unicellular hosts, a wide variety of constitutive or regulatable promoters may be employed. Expression in a microorganism can provide a ready source of the plant enzyme. Among transcriptional initiation regions which have been described are regions from bacterial and yeast hosts, such as *E. coli, B. subtilis, Sacchromyces cerevisiae,* including genes such as beta-galactosidase, T7 polymerase, tryptophan E and the like.

For the most part, the constructs will involve regulatory regions functional in plants which provide for modified production of plant LPAAT, and possibly, modification of the fatty acid composition. The open reading frame, coding for the plant LPAAT or functional fragment thereof will be joined at its 5' end to a transcription initiation regulatory region. In embodiments wherein the expression of the LPAAT protein is desired in a plant host, the use of all or part of the complete plant LPAAT gene is desired; namely all or part of the 5' upstream non-coding regions (promoter) together with the structural gene sequence and 3' downstream non-coding regions may be employed.

If a different promoter is desired, such as a promoter native to the plant host of interest or a modified promoter, i.e., having transcription initiation regions derived from one gene source and translation initiation regions derived from a different gene source, numerous transcription initiation regions are available which provide for a wide variety of constitutive or regulatable, e.g., inducible, transcription of the structural gene functions. The transcription/translation initiation regions corresponding to such structural genes are found immediately 5' upstream to the respective start codons. Among transcriptional initiation regions used for plants are such regions associated with the T-DNA structural genes such as for nopaline and mannopine synthases, the 19S and 35S promoters from CaMV, and the 5' upstream regions from other plant genes such as napin, ACP, SSU, PG, zein, phaseolin E, and the like. Enhanced promoters, such as double 35S, are also available for expression of LPAAT sequences. For such applications when 5' upstream non-coding regions are obtained from other genes regulated during seed maturation, those preferentially expressed in plant embryo tissue, such as ACP and napin-derived transcription initiation control regions, are desired. Such "seed-specific promoters" may be obtained and used in accordance with the teachings of U.S. Ser. No. 07/147,781, filed Jan. 25, 1988 (now U.S. Ser. No. 07/550,804, filed Jul. 9, 1990), and U.S. Ser. No. 07/494,722 filed on or about Mar. 16, 1990 having a title "Novel Sequences Preferentially Expressed In Early Seed Development and Methods Related Thereto," which references are hereby incorporated by reference. Transcription initiation regions which are preferentially expressed in seed tissue, i.e., which are undetectable in other plant parts, are considered desirable for TAG modifications in order to minimize any disruptive or adverse effects of the gene product.

Regulatory transcript termination regions may be provided in DNA constructs of this invention as well. Transcript termination regions may be provided by the DNA sequence encoding the plant LPAAT or a convenient transcription termination region derived from a different gene source, for example, the transcript termination region which is naturally associated with the transcript initiation region. Where the transcript termination region is from a different gene source, it will contain at least about 0.5 kb, preferably about 1–3 kb of sequence 3' to the structural gene from which the termination region is derived.

Plant expression or transcription constructs having a plant LPAAT as the DNA sequence of interest for increased or decreased expression thereof may be employed with a wide variety of plant life, particularly, plant life involved in the production of vegetable oils for edible and industrial uses. Most especially preferred are temperate oilseed crops. Plants of interest include, but are not limited to, rapeseed (Canola and High Erucic Acid varieties), sunflower, safflower, cotton, soybean, peanut, coconut and oil palms, and corn. Depending on the method for introducing the recombinant constructs into the host cell, other DNA sequences may be required. Importantly, this invention is applicable to dicotyledyons and monocotyledons species alike and will be readily applicable to new and/or improved transformation and regulation techniques.

Of particular interest, is the use of plant LPAAT constructs in plants which have been genetically engineered to produce a particular fatty acid in the plant seed oil, where TAG in the seeds of nonengineered plants of the engineered species, do not naturally contain that particular fatty acid. For example, in Brassica plants which have been genetically engineered to produce the medium-chain fatty acids, and in particular laurate (12:0), in the seed oil, a deficiency in sn-2 acylation has been discovered. (See WO 92/20236.) For example, in oil from plants in which 40% of the seed oil fatty acyl groups have been changed from the long-chain (primarily 18:1) type to 12:0, the 12:0 enrichment at the sn-1 and sn-3 positions (averaged together) is approximately 50% and the 12:0-enrichment at the sn-2 position is approximately 12%. Additionally, after separation of the intact triglyceride species by reverse-phase HPLC, it was estimated that only 1% of the triglyceride molecules are tri-12:0, whereas the statistically predicted proportion from random acylation at all three sn positions would be 7%. Thus, the expression of a lauroyl-CoA preferring plant LPAAT in such C12 producing Brassica plants is desirable for enhanced incorporation of 12:0 fatty acyl groups into the sn-2 position.

The coconut medium-chain preferring LPAAT may thus be used for enhancing the incorporation of laurate into storage oil in rapeseed. In addition, production of TAG containing other medium-chain fatty acyl groups in Brassica and other oilseed crop plants is also desired. (See, for example, WO 92/20236). As the coconut LPAAT has significant ability to utilize other medium chain lengths, particularly C10 and C14, it also has the potential to enhance the incorporation of these fatty acids into plant TAG. Furthermore, TAGs having shorter chain fatty acyl groups in all three sn positions are desirable for various medical applications. Such TAG molecules may be obtained by expression of appropriate acyl-ACP thioesterase and LPAAT genes in oilseed crop plants.

Likewise, the expression of any LPAAT which is capable of transferring a medium-chain fatty acyl group into the sn-2 position of an LPA substrate is also desired for applications in crop species engineered to contain medium-chain fatty acids. Preferential activity is not required, so long as the capability of medium-chain utilization is present.

Further plant genetic engineering applications for LPAAT proteins of this invention include their use in preparation of structured plant lipids which contain TAG molecules having desirable fatty acyl groups incorporated into particular positions on the TAG molecules. For example, in Brassica plants, the sn-2 position of TAG contains mainly unsaturated fatty acyl groups. In certain applications, it may be desirable to have saturated fatty acids at the sn-2 position, and thus an LPAAT from a different plant source may be identified as having activity on, for example 16:0 or 18:0 acyl-CoA substrates, and used for transformation of Brassica.

In addition, in Brassica plants which contain high levels of erucic acid (22:1) in their seed oils (high erucic acid rapeseed or HEAR), little or no 22:1 is found in the sn-2 position of the TAG molecules. A "tri-erucic" HEAR plant having 22:1 in all three of the TAG sn positions is desirable. Such a seed oil might be obtained for example by expression of a C22:1 active LPAAT in HEAR plants. A gene encoding such an LPAAT could be obtained from a plant, such as meadowfoam (*Limnanthes alba*), whose seeds accumulate oil containing erucic acid (22:1) in all three sn positions.

The method of transformation in obtaining such transgenic plants is not critical to the instant invention, and various methods of plant transformation are currently available. Furthermore, as newer methods become available to transform crops, they may also be directly applied hereunder. For example, many plant species naturally susceptible to Agrobacterium infection may be successfully transformed via tripartite or binary vector methods of Agrobacterium mediated transformation. In many instances, it will be desirable to have the construct bordered on one or both sides by T-DNA, particularly having the left and right borders, more particularly the right border. This is particularly useful when the construct uses *A. tumefaciens* or *A. rhizogenes* as a mode for transformation, although the T-DNA borders may find use with other modes of transformation. In addition, techniques of microinjection, DNA particle bombardment, and electroporation have been developed which allow for the transformation of various monocot and dicot plant species.

Normally, included with the DNA construct will be a structural gene having the necessary regulatory regions for expression in a host and providing for selection of transformant cells. The gene may provide for resistance to a cytotoxic agent, e.g. antibiotic, heavy metal, toxin, etc., complementation providing prototrophy to an auxotrophic host, viral immunity or the like. Depending upon the number of different host species the expression construct or components thereof are introduced, one or more markers may be employed, where different conditions for selection are used for the different hosts.

Where Agrobacterium is used for plant cell transformation, a vector may be used which may be introduced into the Agrobacterium host for homologous recombination with T-DNA or the Ti- or Ri-plasmid present in the Agrobacterium host. The Ti- or Ri-plasmid containing the T-DNA for recombination may be armed (capable of causing gall formation) or disarmed (incapable of causing gall formation), the latter being permissible, so long as the vir genes are present in the transformed Agrobacterium host. The armed plasmid can give a mixture of normal plant cells and gall.

In some instances where Agrobacterium is used as the vehicle for transforming host plant cells, the expression or transcription construct bordered by the T-DNA border region (s) will be inserted into a broad host range vector capable of replication in *E. coli* and Agrobacterium, there being broad host range vectors described in the literature. Commonly used is pRK2 or derivatives thereof. See, for example, Ditta, et al., (*Proc. Nat. Acad. Sci., U.S.A.* (1980) 77:7347–7351) and EPA 0 120 515, which are incorporated herein by reference. Alternatively, one may insert the sequences to be expressed in plant cells into a vector containing separate replication sequences, one of which stabilizes the vector in *E. coli,* and the other in Agrobacterium. See, for example, McBride and Summerfelt (*Plant Mol. Biol.* (1990) 14:269–276), wherein the pRiHRI (Jouanin, et al., *Mol. Gen. Genet.* (1985) 201:370–374) origin of replication is utilized and provides for added stability of the plant expression vectors in host Agrobacterium cells.

Included with the expression construct and the T-DNA will be one or more markers, which allow for selection of transformed Agrobacterium and transformed plant cells. A number of markers have been developed for use with plant cells, such as resistance to chloramphenicol, kanamycin, the aminoglycoside G418, hygromycin, or the like. The particular marker employed is not essential to this invention, one or another marker being preferred depending on the particular host and the manner of construction.

For transformation of plant cells using Agrobacterium, explants may be combined and incubated with the transformed Agrobacterium for sufficient time for transformation, the bacteria killed, and the plant cells cultured in an appropriate selective medium. Once callus forms, shoot formation can be encouraged by employing the appropriate plant hormones in accordance with known methods and the shoots transferred to rooting medium for regeneration of plants. The plants may then be grown to seed and the seed used to establish repetitive generations and for isolation of vegetable oils.

The invention now being generally described, it will be more readily understood by reference to the following examples which are included for purposes of illustration only and are not intended to limit the present invention.

EXAMPLES

Example 1
Assay for LPAAT Activity
A. Assay for LPAAT Activity in Cell-free Homogenates and Membrane Preparations To assay for LPAAT activity, the sample is incubated with lysophosphatidic acid (LPA) and acyl-coenzyme A (acyl-CoA) substrates in buffered solution. The acyl substituents of the two substrates are chosen to correspond with the specificity of the enzyme being measured. For example, to measure activity of an LPAAT having preference for medium-chain substrates, lauroyl-LPA (lauroyl-lysophosphatidic acid) and lauroyl-CoA may be used, and to measure activity of an LPAAT preferring longer-chain acyl groups, oleoyl-LPA and oleoyl-CoA may be used. The acyl group of one substrate is radioactively labeled in order to detect the product formed. In the examples which follow the acyl substituent of the acyl-CoA substrate is radiolabeled with $^{14}C$ in the carboxyl group. LPAAT activity results in transfer of this acyl group from the acyl-CoA "donor" substrate to the LPA "acceptor" substrate, converting the latter into the product, phosphatidic acid (PA). LPAAT activity is measured as the amount of radioactive product formed in a given assay time. The PA product is radioactive as a result of the transferred radiolabeled acyl group at the central carbon atom of the molecule, and the quantity of PA formed may be determined by measuring radioactivity of the PA fraction. For this measurement, the PA is first separated from the acyl-CoA substrate by solvent partitioning, or by thin-layer chromatography (TLC).

Acyl[1-$^{14}C$]-CoA substrates can be purchased from commercial suppliers, such as Amersham (Arlington Heights, Ill.). Acyl[1-$^{14}C$]-CoA substrates which cannot be purchased from commercial suppliers (e.g. lauroyl[1-$^{14}C$]-CoA) may be synthesized enzymatically using the method of Taylor et al. (*Analyt. Biochem.* (1990) 184:311–316). The [1-$^{14}C$]fatty acids used in the synthesis typically have specific radioactivities of 20 Ci/mol. The radiolabeled acyl-CoA substrate is diluted before use to 12.5 μM and stored in 3 mM sodium acetate (pH 4.8). Oleoyl-LPA is obtained from commercial suppliers, and lauroyl-LPA is enzymatically synthesized using the method of Ichihara et al. (*Eur. J. Biochem.* (1987) 167:339–3457), based on the use of phospholipase D to cleave choline from commercially available lauroyl-lysophosphatidylcholine.

20 μl of the sample to be assayed for LPAAT activity is mixed with 217.5 μl of an assay ingredient mixture in a 4-ml, screw-cap vial. The components of this mixture are adjusted such that after substrate addition as described below, the final 250 μl assay system will contain: 100 mM HEPES-NaOH (pH 7.5) (HEPES=N-[2-hydroxyethyl]piperazine-N'[2-ethanesulfonic acid], 200 mM NaCl, 4% glycerol (v/v), 10 mM EDTA (ethylenediaminetetra-acetate, disodium salt), 5 mM β-ME (β-mercaptoethanol). The LPA substrate is then added (2.5 μl) to provide a final concentration of 20 μM. Control samples to determine nonenzymatic background "activity" can be prepared by omitting the LPAAT sample or the LPA. The assay incubation is started by addition of 10 μl of the 12.5 mM radiolabeled acyl-CoA solution so that the final concentration is 5 μM. If acyl-CoA concentrations vary slightly from 12.5 mM the 10 μl volume is changed accordingly to achieve 5 μM final concentration, and the volume change accommodated by adjusting the water content of the assay mixture so that the total volume and all concentrations remain unchanged. The incubation takes place in a water bath at 300°, for 20–30 minutes.

To stop the assay, 0.25 ml of 1M KCl in 0.2M $H_3PO_4$ is added to the vial. At this point, 40 μl BSA (bovine serum albumin, fraction V) at 1 mg/ml are added, followed by 0.75 ml of a solution of 67 μg/ml unlabeled PA (acting as a "carrier" to facilitate partitioning) in chloroform/methanol (2:1, v/v). The chain lengths of the PA acyl groups are chosen to correspond to those used in the assay substrates. Upon thorough mixing of these components the radiolabeled PA product of the LPAAT reaction partitions into the organic phase and away from the unreacted acyl-CoA and LPA. The vial is centrifuged briefly at low speed to facilitate the separation of organic (lower) and aqueous (upper) phases. The aqueous phase is then removed and discarded. The total radioactivity extracted into the organic phase is determined by liquid scintillation counting; a 100 μl sample of the organic phase is transferred to a 20 ml scintillation vial and allowed to dry, and scintillation fluid (3–5 ml) is added to the vial. The radioactivity of the sample, after subtraction of the "minus-enzyme" or "minus-LPA" radioactivities, is taken as an approximate indication of the amount of PA formed in the LPAAT-catalyzed reaction and therefore of LPAAT activity.

The determination is an approximation due to the presence of non-PA radioactivity in the organic extract. The non-PA radioactivity results from the partitioning of a small amount of the radiolabeled acyl-CoA substrate into the organic layer along with certain impurities in the acyl-CoA (deriving from impurities in the original radioactive fatty acid used in its preparation), and any free fatty acid resulting from acyl-CoA hydrolysis that may take place.

A more accurate estimation of the LPAAT activity may be obtained by separating the PA product from these contaminants by TLC. The remaining organic phase is applied to a silica TLC plate. Ascending chromatography is carried out for 50 minutes, using the solvent mixture chloroform/pyridine/88% formic acid (50:30:7, v/v). After the plate has dried, the distribution of radioactivity is visualized and quantitated using an AMBIS radioanalytic imaging system (AMBIS Systems Inc., San Diego, Calif.). From prior application of standard lipid components the Rf of the PA is known. The radioactivity associated with the PA spot is expressed as a percentage of the total radioactivity of the assay sample loaded on the plate. This ratio provides an indication of the proportion of the scintillation counts which represent the PA product, and may be used to correct the counts to obtain the total PA radioactivity formed in the assay.

For a given LPAAT enzyme source, the effects of incubation time and sample concentration on LPAAT activity are determined to define the conditions under which the assay results (PA radioactivity) provide a linear measure of LPAAT activity. Subsequent assays are then conducted within the determined limits.

B. Assay for LPAAT Activity Following Solubilization

After solubilization of LPAAT protein from plant membranes as described below, modification of the above assay conditions are required in order to detect maximum LPAAT activity. This is especially important after the solubilized LPAAT has been chromatographed on at least one column. The important modification to the assay is the addition, at the start of the assay procedure, of 1 μl of a concentrated phospholipid (PL) solution to 20 μl of the LPAAT-containing sample in a glass vial. The high concentrations of CHAPS (at least 1% w/v) and NaCl (typically 0.5M or greater) in the solubilized LPAAT preparation aids in dispersal of the phospholipids. The phospholipid solution is obtained by sonicating crude soybean phospholipids (L-phosphatidylcholine from soybean, "Type IVs" obtained from Sigma Chemical Company, St. Louis) at 50 mg/ml in 0.5% (w/v) CHAPS (3-[(3-cholamidopropyl)-dimethylammonio]-1-propane-sulfonate) until a uniform suspension is obtained. Synthetic phospholipids (phosphatidyl choline, inositol, or ethanolamine alone or in combination), and turkey egg yolk phospholipid preparation, do not offer significant improvement over the crude soybean material.

The remaining assay ingredients (as described above), with the exception of the acyl-CoA substrate, are then added as 219 μl of a mixture. By this addition, the CHAPS and NaCl are diluted to levels which do not hinder enzyme activity, but the solution does not turn cloudy, which suggests that the phospholipids remain dispersed. Radiolabeled acyl-CoA (10 μl, or an appropriately adjusted volume as indicated above) is added to start the LPAAT-catalyzed reaction and the rest of the assay procedure is completed as described above.

The effect of the timing of addition of phospholipids in the assay described above is illustrated in the following table:

| Stage of PL addition | LPAAT Activity (cpm) |
|---|---|
| At start of assay (control) | 914 |
| None added | 0 |
| At start of incubation | 231 |
| At end of incubation | 0 |

These results demonstrate that the stimulatory action of the phospholipids is greatest when they are added to the LPAAT preparation at the start of the assay procedure, prior to dilution of the CHAPS and NaCl concentrations by addition of the other assay ingredients. Addition of phospholipids after this dilution, or just prior to the addition of partitioning mixture (chloroform/methanol etc.), is less effective or ineffective.

To determine whether this sequence of phospholipid addition is more important for the LPAAT enzyme or for the phospholipids, a second experiment is conducted in which a purified LPAAT preparation (S3 preparation that has been purified sequentially on red 120 agarose and hydroxyapatite columns, Example 5 below) is added just prior to the start of the incubation. In this experiment, the phospholipids are first mixed with Solubilization Buffer and subsequently diluted with the assay components prior to addition of LPAAT activity.

The results demonstrate that the activity obtained by adding the LPAAT preparation just prior to incubation is identical to that obtained when the phospholipids are added at the start of the assay. It is therefore the treatment of the phospholipids, in exposing them to high CHAPS and NaCl concentrations and then diluting the mixture, that is critical in order to obtain their activation of LPAAT. The final LPAAT activity depends on the phospholipid concentration used, increasing up to 20 μg phospholipid/assay and remaining unchanged from 20 to 50 μg phospholipid/assay. This dependance on phospholipid concentration is independent of S3 concentration. These observations are summarized in FIG. 1.

In the following examples, where solubilized and column-chromatographed coconut LPAAT preparations are implicated, the assay data refer to this modified assay method involving the use of soybean phospholipids.

It is not possible to activate the solubilized bay long-chain LPAAT in this way to obtain maximal activity; when the phospholipids are included in the bay assay an alternative reaction occurs, diverting the radiolabeled acyl group from the 18:1-CoA to another product distinguishable from the LPAAT product (PA) by TLC.

Example 2

Preparation of Cell-free Homogenates and Membrane Fractions with LPAAT Activity

A. Coconut LPAAT

Coconuts (*Cocos nucifera*) are obtained from local supermarket stores. For maximum yield of LPAAT activity, immature coconuts referred to as "green", which have a very pale brown or white endocarp (exterior "shell") are used. The endocarp of the coconut is pierced and the "milk" liquid within the hollow interior drained and discarded. The coconut is then broken into fragments so that the white endosperm tissue lining the inside of the endocarp can be dissected and collected. The brown testa between the endosperm and the endocarp is removed and discarded, and the endosperm is frozen by immersion in liquid nitrogen and stored at −70° C. for future use. In a typical preparation as described below, 24 g of tissue are processed. As individual coconuts may vary considerably with respect to the maturity of the endosperm and therefore the yield of obtainable LPAAT, the endosperm may be sampled to assess the LPAAT content prior to beginning a 24 g-scale preparation. Such a sampling may be accomplished by cutting a hole in the endocarp, approximately 1 inch in diameter. The resulting disc of endosperm is dissected away from the testa and endocarp and processed as described below except that 16 ml Extraction Buffer are used for analysis of a 2 g powdered endosperm sample.

Frozen coconut endosperm tissue is powdered by impact crushing in a steel mortar and pestle in liquid nitrogen. The powder from 24 g of tissue is added to 144 ml Extraction Buffer at 0–4° C., and the mixture is blended with a Polytron tissue homogenizer to make a cell-free homogenate. Extraction Buffer contains 50 mM HEPES-NaOH (pH 7.5), 3M NaCl, 10 mM EDTA, 10 mM DIECA (diethyldithiocarbamic acid, sodium salt), 100 μM Pefabloc (protease inhibitor available from Sigma Chemical Co.), 1 μM leupeptin, 0.1 μM pepstatin A, 5 mM β-ME. All subsequent steps are performed at 4° C.

The homogenate is filtered through 4 layers of cheesecloth which has been wetted with Extraction Buffer. The remaining solids are enfolded in the cheesecloth and the cheesecloth wrung to extract more liquid. The cheesecloth is then unfolded, the solids wetted with 48 ml of Extraction Buffer, and the cheesecloth wrung again. The resulting filtrate is centrifuged at 12,000× g for 30 minutes. The resulting sample contains a floating fat pad and a pellet, which are both discarded, and a supernatant fraction (S1). The supernatant fraction is filtered to remove residual solids using Miracloth (Calbiochem; La Jolla, Calif.) which has been wetted with Extraction Buffer. This S1 fraction is then dialyzed overnight against 4 liters of Dialysis Buffer (50 mM HEPES-NaOH pH 7.5, 1M NaCl, 5 mM β-ME), with one change of buffer. Dialysis membrane having a molecular weight cutoff of 12,000–14,000 is used. The dialyzed S1 material (DS1) is then centrifuged at 12,000× g for 30 minutes and the supernatant fraction again filtered through buffer-wetted Miracloth.

The DS1 supernatant is then centrifuged at 100,000× g for 2 hours. The resulting sample contains a pelleted fraction containing subcellular membranes (P2), and a supernatant fraction which is discarded. Residual supernatant fraction is removed from the P2 fraction by draining the centrifuge tubes and wiping with paper tissues.

P2 Buffer (100 mM HEPES-NaOH (pH 7.5), 200 mM NaCl, 20% glycerol (w/v), 10 mM EDTA, 5 mM β-ME) is added to the P2 pellets so that when the mixture is transferred to a ground glass homogenizer and homogenized, the total volume of the homogenate will be 2.5 ml. The P2 homogenate is divided into aliquots, frozen in liquid nitrogen, and stored at −70° C. for future use.

B. California bay LPAAT

A P2 membrane homogenate from immature cotyledons of developing California bay (*Umbellularia californica*) seeds is prepared essentially as described above, except as noted below. The seeds are dissected, and the pale green cotyledons are removed, frozen in liquid nitrogen and stored at −70° C. The frozen bay tissue is powdered in liquid nitrogen as described above. Typically 20 g of powdered embryo tissue are homogenized with Modified Extraction Buffer (100 mM HEPES-NaOH pH 7.5, 3M NaCl, 10 mM DIECA, 100 μM PMSF (phenylmethylsulfonyl fluoride), 1 μM leupeptin, 0.1 μM pepstatin A) in a final volume of 200 ml. The homogenate is centrifuged at 10,000× g for 15 minutes, yielding a floating fat pad and a pellet, which are both discarded, and a supernatant fraction (S1).

The S1 fraction is centrifuged at 100,000× g for 90 minutes, yielding a supernatant fraction and a pellet (P2). The P2 pellet, which contains subcellular membranes, is resuspended in approximately 30 ml of Modified Extraction Buffer, and centrifuged again at 100,000× g for 90 minutes. The resulting pellet (P3) is resuspended in approximately 2 ml Modified P2 Buffer (100 mM HEPES-NaOH (pH 7.5), 200 mM NaCl, 5% glycerol (w/v), 10 mM EDTA). The suspension is then divided into aliquots, frozen in liquid nitrogen and stored at −70° C. for future use.

C. Rapeseed LPAAT

A P2 membrane homogenate from immature embryos of developing rapeseed (*Brassica napus*) seeds is prepared essentially as described above, except as noted below. Immature Brassica seeds are harvested from plants grown in growth chambers and greenhouses. The embryos are dissected from the immature seeds and frozen in liquid nitrogen. Approximately 1.66 g of Brassica embryos are ground in 8 ml Modified Extraction Buffer using a chilled mortar and pestle. Since little starting tissue is used, the homogenate is not filtered through cheesecloth, but is centrifuged at 10,000× g for 50 minutes. The supernatant fraction (S1) is then centrifuged at 100,000× g for 2 hours, and the resulting membrane-containing P2 pellet is resuspended in 0.25 ml Modified P2 Buffer, frozen in liquid nitrogen, and stored at −70° C. for future use.

Example 3

Characterization of LPAAT Activity in Cell-free Homogenates and P2 Membrane Preparations A. Enzyme Activity Coconut, bay, and rapeseed cell-free homogenates and P2 membrane preparations all display LPAAT activity as measured by the assay described in Example 1A. LPAAT activity is dependent on assay incubation time and varies with the concentrations of substrates and P2 preparation, as expected for enzyme catalysis. Confirmation of the identity of the reaction product as PA can be obtained by incubating the product with phospholipase A2 (available commercially, e.g. purified from *Crotalus atrox* venom). Radioactivity is converted to a form which migrates on TLC as free fatty acid. As phospholipase A2 removes the fatty acyl group at the sn-2 hydroxyl substituent of PA, this result is consistent with the radioactive LPAAT product being PA radiolabeled at the sn-2 position.

B. Substrate Specificity

The LPAAT activity involved in triacylglycerol (seed oil) biosynthesis is associated with the cytoplasmic endoplasmic reticulum membranes (sometimes referred to as "microsomes") and prefers acyl-CoAs over acyl-ACPs as donor substrates. A functionally analogous enzyme which is able to utilize both acyl-ACP and acyl-CoA substrates is present in plant plastids (Harwood, in Crit. Rev. Plant Sci. (1989), vol. 8, pp. 1–43). The coconut P2 preparation will not utilize 12:0-ACP as the LPAAT donor substrate instead of 12:0-CoA. This indicates that the coconut P2 preparation contains the cytoplasmic type of LPAAT appropriate to seed oil biosynthesis. The same assay shows that the 12:0-ACP is not hydrolyzed by the P2 preparation, which demonstrates that the lack of 12:0-ACP utilization by coconut LPAAT is not a result of depletion of 12:0-ACP by hydrolysis. Similarly, the bay P2 preparation will not significantly utilize 18:1-ACP as the LPAAT donor substrate instead of 18:1-CoA. Thus, the bay P2 preparation also contains the endoplasmic reticulum type of LPAAT appropriate to seed oil biosynthesis.

Lysophosphatidylcholine (LPC) acyltransferase (LPCAT) is an enzyme analogous to LPAAT, involved in the biosynthesis of membrane lipids (phosphatidyl choline and derivatives thereof) instead of storage oil. The possibility that the activity measured in the LPAAT assay is not true LPAAT, but rather an inefficient action of LPCAT on the LPAAT substrates, can be tested by direct assay for LPCAT. For example, the LPAAT activity of the coconut P2 preparation with the substrate combination 12:0-CoA+12:0-LPA is readily measurable, whereas the LPCAT activity of the same preparation with the substrates 12:0-CoA+12:0-LPC is undetectable. This indicates that the measured medium-chain LPAAT activity is due to an LPAAT enzyme, and not due to an inefficient, side-reaction of LPCAT. When the substrates all have 18:1 acyl groups the activities in the LPAAT and LPCAT assays (coconut or bay P2 preparations) are of comparable magnitude. The activities on long-chain substrates may represent either a single acyltransferase enzyme able to use LPA and LPC acceptor substrates, or discrete "long-chain" LPAAT and LPCAT enzymes which are present together.

C. Chain-length Specificity

The LPAAT activities of the P2 membrane preparations are further characterized with respect to chain-length preference for the donor and acceptor substrates. The following table presents results of LPAAT activity analysis of P2 membrane preparations from coconut, bay, and rapeseed. LPAAT activity is measured with using a variety of acyl-CoA donor substrates, with the acceptor substrate held constant as 12:0-LPA.

| Donor (Acyl-CoA) Substrate | LPAAT Activity* from: | | |
|---|---|---|---|
| | Coconut | Bay | Rapeseed |
| 6:0 | 3 | 1 | 0 |
| 8:0 | 6 | 13 | 2 |
| 10:0 | 43 | 10 | 12 |
| 12:0 | 238 | 14 | 79 |
| 14:0 | 61 | 5 | 16 |
| 16:0 | 21 | 6 | 27 |
| 18:0 | 13 | 6 | 21 |
| 18:1 | 9 | 5 | 218 |

*pmol PA formed/30 min assay

The coconut LPAAT activity demonstrates a dramatic preference for 12:0-containing donor substrate, and also readily utilizes additional medium-chain donor acyl-CoA substrates (10:0- and 14:0-containing acyl-CoA substrates). The bay LPAAT activity when 12:0-LPA is the acceptor substrate demonstrates a preference for medium-chain acyl-CoA substrates (8:0-, 10:0- and 12:0-containing). Rapeseed LPAAT prefers the 18:1 donor when 12:0-LPA is the acceptor, in agreement with previous characterizations.

Similar acyl-CoA preferences are observed when assaying coconut LPAAT activity with 18:1-LPA as the acceptor substrate. However, due to differences in substrate kinetics for 12:0-LPA and 18:1-LPA, direct comparisons of LPAAT activity on different acceptor substrates using a single acyl-CoA donor substrate are difficult to make.

In the examples which follow, "medium-chain" LPAAT refers to activity assayed with 12:0-CoA and 12:0-LPA substrates, and "long-chain" LPAAT refers to activity assayed with 18:1-CoA and 18:1-LPA substrates.

D. Other Properties

Using the bay P2 membrane preparation, many detergents are found to be inhibitory when included in the assay. For example, a long-chain LPAAT activity (18:1-CoA and 18:1-LPA as substrates) in bay P2 preparations is inhibited completely by 0.1% (all concentrations quoted as w/v) octyl glucoside, 0.002% SDS (sodium dodecyl sulfate), 0.005% Zwittergent 3–14 (Calbiochem), 1% Tween 20 or Brij 35, 0.03% Triton X100, and by 0.1% sodium deoxycholate. Exposure of the P2 preparation to higher concentrations than these is possible without permanent loss of enzyme activity, provided the enzyme-plus-detergent mixture is diluted prior to assay to reduce the detergent concentration to a level which is tolerated. For example, the bay P2 preparation can be subjected to a 1-hour exposure to 1.25% Brij 35, 0.5% octyl glucoside, 0.1% Triton X-100, or 2.5% Tween 20 without complete loss of activity, provided the preparation is diluted prior to assay to reduce these detergent concentrations (to 0.025, 0.01, 0.002, and 0.05% respectively).

The detergent CHAPS, used for solubilization as described in the examples which follow, is inhibitory in the coconut medium-chain LPAAT assay at concentrations above 0.1% (w/v). Accordingly CHAPS-solubilized LPAAT must be assayed after dilution to reduce the CHAPS concentration to at least 0.1%. Prior exposure of the coconut P2 preparation to higher CHAPS concentrations, such as 0.5% (w/v), is possible with only partial LPAAT activity loss (50% in this example), provided the dilution is undertaken prior to assay. This phenomenon of tolerance of higher detergent concentrations than can be accepted in the assay provides a basis for screening for solubilization conditions.

The coconut, P2, medium-chain LPAAT activity is unaffected by 0.1 mM CoA, 2 mM adenosine-5'-triphosphate, or 60 $\mu$M lysophosphatidylcholine in the assay system.

The long-chain LPAAT activity of the bay P2 preparation varies with pH in the assay, being detectable between pH 6 and 10, high between pH 7 and 9, and maximal at pH 8. The medium-chain LPAAT activity of the coconut P2 preparation also shows little change when the assay is ranged between pH 6.5 and 8.5 (in 0.5 pH increments), and there is a slight preference for pH 8.0.

Example 4

Solubilization of LPAAT Activity

A. Coconut Medium-chain and Bay Long-chain LPAATs

All steps are carried out at 0–4° C. The frozen coconut P2 preparation is thawed and diluted in a volume of P2 Buffer to achieve a protein concentration of 0.94 mg/ml P2 protein. Protein concentration is determined by Coomassie dye staining relative to a bovine serum albumin standard. The P2 membrane suspension is then diluted with an equal volume of Solubilization Buffer (50 mM HEPES-NaOH, pH7.5, 1.8M NaCl, 20% (w/v) glycerol, 4.5% (w/v) CHAPS, 100 $\mu$M Pefabloc, 1 $\mu$M leupeptin, 1 $\mu$M Pepstatin A, and 5 mM β-ME), resulting in final concentrations of 1M NaCl, 2.25% (w/v) detergent, and 0.47 mg/ml protein. These component concentrations, and the resulting detergent/protein ratio of 48/1 (w/w), are important for optimal solubilization. The preparation is then incubated on ice for 30 minutes with occasional, gentle stirring, followed by centrifugation at 252,000× g for 2 hours. The resulting supernatant fraction (S3) is filtered through buffer-wetted Miracloth, and may then be stored frozen (−70) with only slight loss of activity. Optimally, it is applied to chromatography columns without an intervening freeze-thaw cycle.

The bay long-chain LPAAT activity in the bay P2 membrane sample is solubilized in the same manner, with the Solubilization Buffer CHAPS and NaCl concentrations being 4% (w/v) and 1M respectively, and the detergent/protein ratio being 58/1 (w/w).

The detergent BIGCHAP (N,N-bis[3-D-gluconamidopropyl]-cholamide) may also be substituted for CHAPS in solubilization of either bay or coconut LPAAT, provided the BIGCHAP concentration in the final mixture is 4% (w/v) and a larger portion of the P2 preparation is used so that the detergent/protein ratio is unchanged.

B. Evidence for Solubilization

"Solubilization" refers to extraction of the LPAAT enzyme from the membranes present in the P2 preparation, in such a way that it then behaves in a manner typical of enzymes that are not membrane-associated. In testing for solubilization of LPAAT activity, the following indications of solubilization are considered:

1) LPAAT activity is not sedimented by high-speed centrifugation equivalent to, or of larger, g force than that used to sediment the P2 membranes.
2) LPAAT activity migrates on a size-exclusion chromatography column as though it had a native molecular weight typical of enzymes which are not membrane-associated.
3) Proteins present in the LPAAT preparation will be at least partially separable from each other by column chromatography.

Preparation of the coconut and bay S3 sample having LPAAT activity involves centrifugation at much greater g force (252,000× g) than was used to prepare the original P2 material (100,000× g). A substantial proportion (up to 79%) of the LPAAT activity is found in the resulting supernatant fraction (S3 preparation), thereby satisfying the first indication of solubilization.

Figure 2:
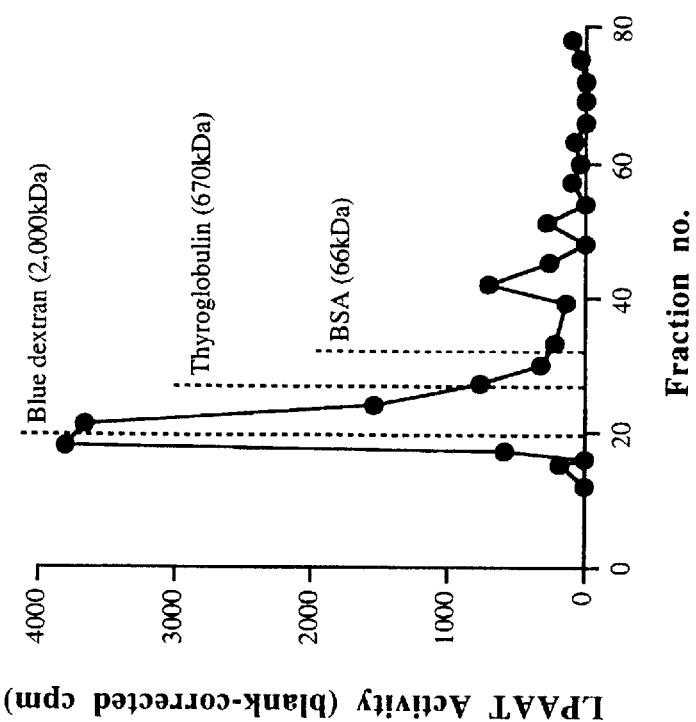
FIG. 2 shows the results of chromatography of bay P2 preparation on Sephacryl S400 column.
Figure 3:
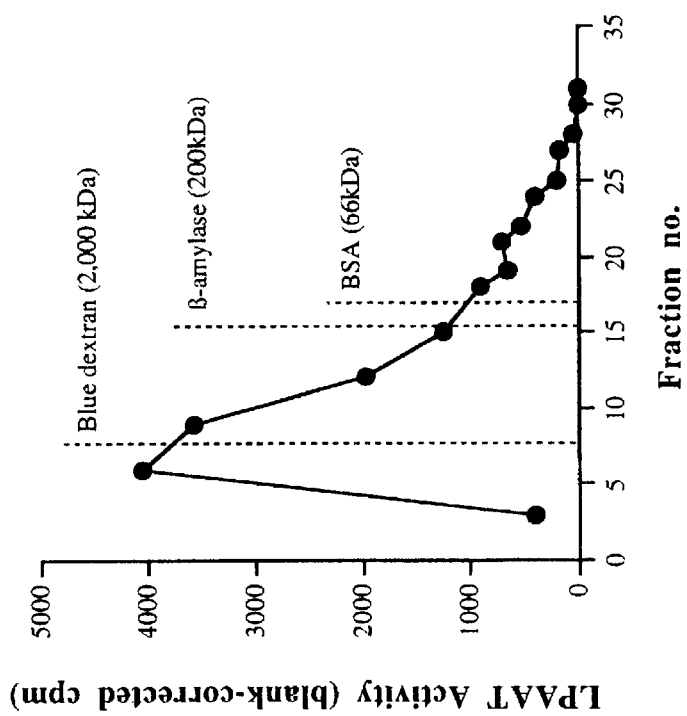
FIG. 3 shows the results of a bay supernatant fraction prepared according to Frentzen et al., and chromatographed on a Sephacryl S400 column.
Figure 4:
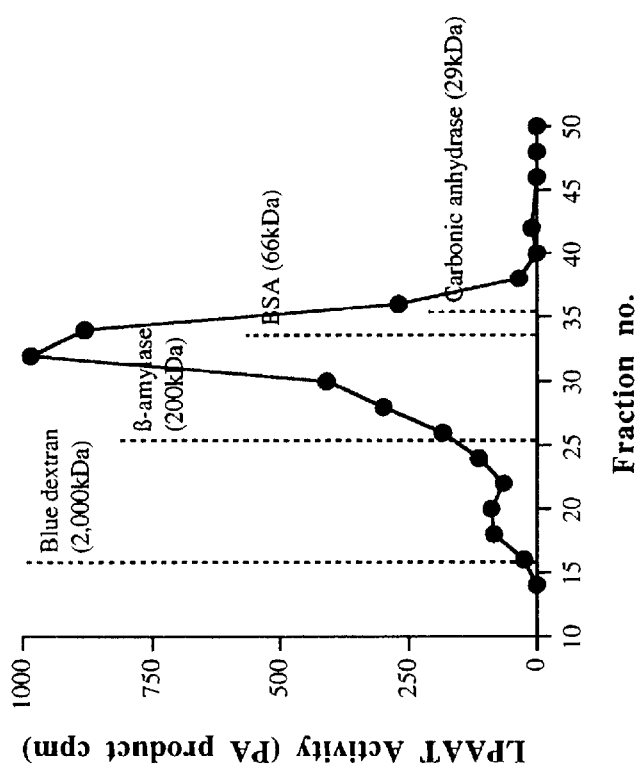
FIG. 4 shows the results of chromatography of the bay S3 preparation on a Superose 6 column.

FIGS. 2–4 show size-exclusion chromatography of the bay long-chain LPAAT activity, using on-column conditions appropriate to the composition of the LPAAT preparation being applied. As shown in the first graph (FIG. 2), the LPAAT activity of the bay P2 preparation passes through a Sephacryl S400 size-exclusion column in the manner of a solute having extremely high molecular weight. The use of high-molecular-weight dye to calibrate the column (peak fraction indicated by dotted line labeled "Blue dextran") indicates that the P2 LPAAT activity migrates without penetration into the porous beads of the column, i.e. in the "excluded" or "void" volume. This is typical of enzyme activities associated with membrane fragments. The second graph (FIG. 3) shows the Sephacryl S400 behavior of bay long-chain LPAAT which is prepared from P2 material according to the "solubilization" procedure for pea shoot LPAAT, published by Hares and Frentzen (*Planta* (1991) 185:124–131). This procedure solubilizes the bay embryo LPAAT according to the first indication based on centrifugation. However, it does not lead to significant LPAAT activity which chromatographs as a protein of low molecular weight on a size-exclusion column. Most of the activity continues to elute from the column with very high molecular weight characteristic of membrane fragments. This observation serves to illustrate that the centrifugation criterion alone is insufficient evidence for solubilization.

In contrast, the LPAAT activity of the bay S3 preparation migrates more slowly through a size-exclusion column and emerges after a larger volume of buffer has passed through, as shown in FIG. 4. (In the example shown a Superose 6 column is used, to enable finer resolution of proteins in the 12–200 kDa range). This behavior is typical of enzymes where the protein molecules are in free solution, not associated with membrane fragments. From the elution volumes of various enzymes used for test purposes (indicated by dotted lines on the graph) it is possible to calibrate the column, and to conclude that the LPAAT activity of the S3 preparation behaves as though it is a globular protein with an approximate molecular weight of 80 kDa. Since most enzymes which are not associated with membranes possess molecular weights in the range 20–100 kDa, this "apparent molecular weight" is consistent with the conclusion that the LPAAT has been solubilized. Closely similar results are obtained with the coconut S3 preparation (assaying medium-chain activity), except that the apparent molecular weight is estimated as 44–50 kDa.

Examination of the protein composition of effluent fractions from such size-exclusion chromatography of the coconut preparation, by SDS-PAGE (polyacrylamide gel electrophoresis), shows that many proteins are present. But the composition varies as fractions are examined from one end of the LPAAT activity peak to the other. Such protein fractionation would not be possible if the P2 membranes had not been dispersed into their individual lipid and protein constituents, i.e. solubilized. Additional evidence of protein resolution is obtained from application of other types of chromatography to the S3 preparation, as in the examples which follow in the section on purification. Furthermore, by means of additional chromatography it is possible to recognize individual proteins as candidate proteins for the LPAAT enzyme. This observation provides evidence that the LPAAT protein itself is amongst those which are dissociated from the membrane in the solubilization procedure.

C. Properties of Solubilized Coconut LPAAT

Figure 5:
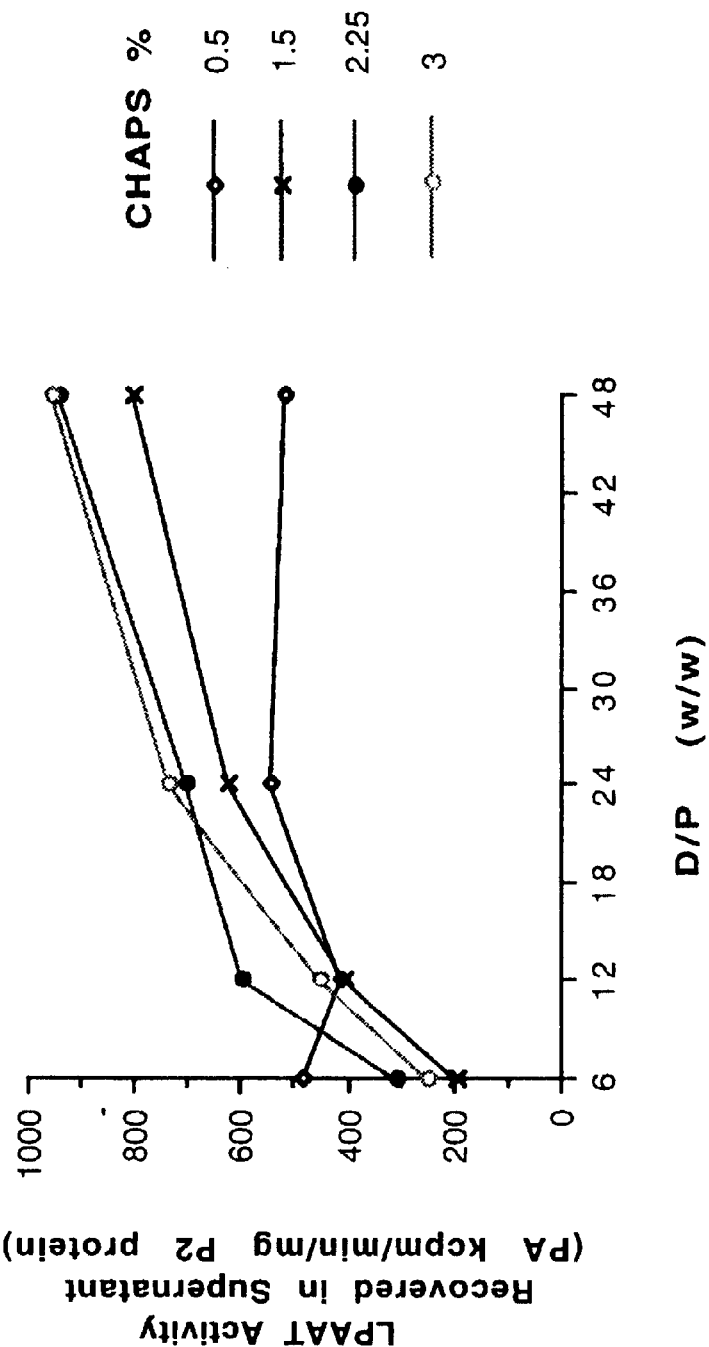
FIG. 5 provides a demonstration of the effects of solubilization by CHAPS concentration and detergent/protein (D/P) ratio, as measured by the yield of coconut medium-chain LPAAT activity in the S3 preparation.

Varying the CHAPS and NaCl concentrations, and the detergent/protein ratio (D/P, w/w), of the solubilizaton procedure results in varying degrees of conversion of coconut medium-chain LPAAT activity from the P2 preparation to the S3 preparation (i.e. on solubilization as defined by the centrifugation criterion). FIG. 5 summarizes the effects of CHAPS concentration (at 1M NaCl) and detergent/protein ratio (D/P, w/w). Lowering the solubilization NaCl concentration below 1M reduces the formation of S3 LPAAT activity (data not shown in figure). The routine solubilization conditions are chosen by selecting the minimum CHAPS concentration for maximal effect (2.25% w/v), and the most effective D/P ratio (48/1 w/w).

Re-examination of the substrate specificity shows that after solubilization and phospholipid-activation coconut LPAAT (S3 preparation) has the same preference for medium-chain acyl-CoAs as the original P2 activity. Also preserved is the comparable use of 12:0-LPA and 18:1-LPA as acceptor substrates. Assay of the coconut medium-chain LPAAT activity after solubilization (S3 preparation) and reactivation with PLs, using different acyl-CoA substrates, provides the following results. In all these assays the acceptor substrate is 12:0-LPA.

| Acyl-CoA | LPAAT Activity* |
| --- | --- |
| 6:0 | 1 |
| 8:0 | 16 |
| 10:0 | 162 |
| 12:0 | 205 |
| 14:0 | 84 |
| 16:0 | 18 |
| 18:1 | 30 |

*Radioactivity (cpm) of PA product resolved on TLC, after 30 min assay.

Comparing these results with the P2 membrane activities, it is seen that the PL-reactivated, solubilized (S3) activity retains the preference for medium-chain acyl-CoAs.

Increasing the EDTA concentration to 10 mM does not affect the LPAAT activity of the coconut S3 preparation. The additions of 1 mM $Mg^{2+}$, $Mn^{2+}$, or $Ca^{2+}$ are also without significant effect, but the activity is reduced by 50% or more if these ions are added at 10 mM. Omitting β-ME from the assay system results in approximately 50% less LPAAT activity, and concentrations above 5 mM also reduce activity. Lowering the assay pH from 7.7 to 6.5 results in a loss of approximately 20% of the LPAAT activity. Raising the pH to 8.0 results in a very slight increase of activity which diminishes again as the pH is raised further to 8.5. The optimum pH is therefore 8.0, but 7.5 is used routinely to minimize nonenzymatic hydrolysis of acyl-CoAs. There is little change in the activity when the assay concentration of NaCl is varied between 100 mM and 200 mM, but activity declines steeply as the NaCl concentration is raised above 200 mM. Activity is insensitive to changes in glycerol concentration in the assay between 5% and 15% (w/v).

Overnight dialysis of the coconut S3 preparation to remove NaCl results in loss of half of the LPAAT activity. The equivalent NaCl removal using a size-exclusion column results in total activity loss. Stability of the coconut S3 preparation during storage at 4° C. is considerably improved once it has been activated with phospholipids.

Example 5
Purification of Coconut Medium-Chain LPAAT

Substantial purification of LPAAT activity relative to the total protein content of the coconut S3 preparation can be obtained by sequential chromatography on columns of red 120 agarose and hydroxyapatite, as follows. The following steps are conducted at 0–4° C. for optimal recovery of LPAAT activity.

A. Red 120 Agarose Chromatography

Figure 6:
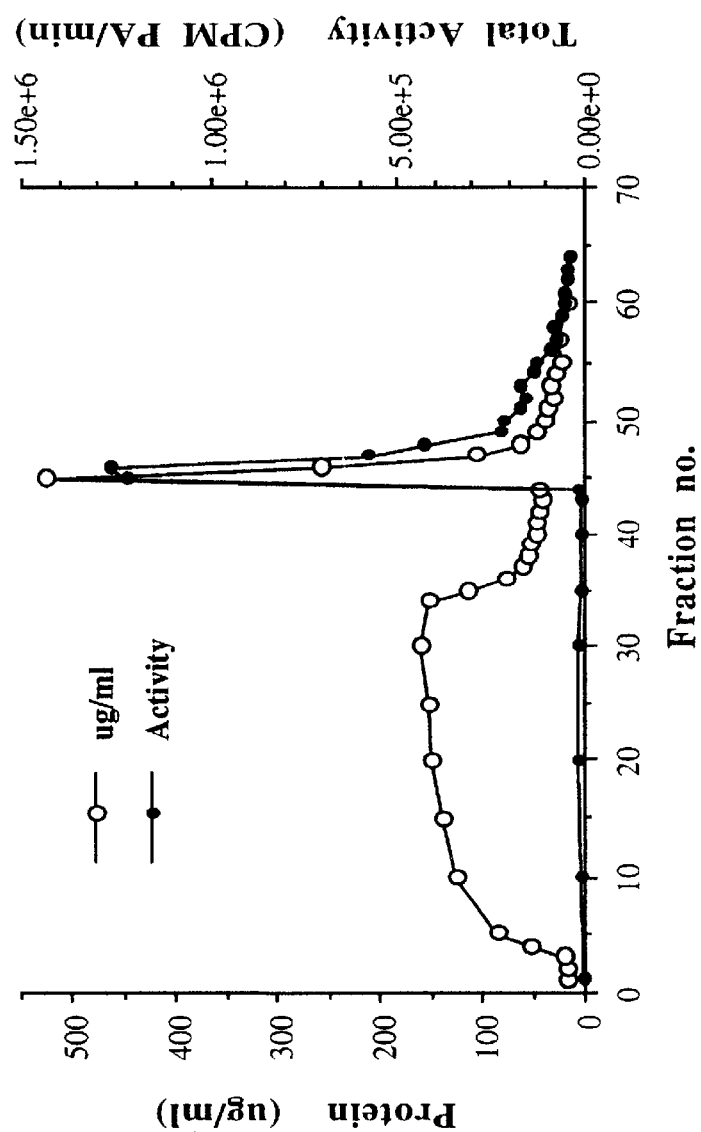
FIG. 6 shows the chromatography of coconut S3 preparation on red 120 agarose.

The S3 preparation is diluted to reduce the CHAPS concentration to 1.125% (w/v) and the NaCl concentration to 0.5M, all other conditions remaining the same. It is then applied at 0.5 ml/min to a 2.5 cm (diam.)×2 cm column of red 120 agarose (Sigma Chemical Co., St. Louis) pre-equilibrated in running buffer containing 50 mM HEPES-NaOH, pH 7.5, 20% (w/v) glycerol, 1% (w/v) CHAPS, 1M NaCl, 5 mM β-ME. Fractions of 3 ml volume are collected. As shown in FIG. 6, LPAAT activity is retained by the column while considerable non-LPAAT protein (assayed by the Coomassie dye method) flows through.

The LPAAT activity is eluted by applying running buffer in which the NaCl concentration is adjusted to 2.5M. A sharp peak of protein accompanies the eluted activity. The LPAAT activity recovery from this procedure is typically close to 100%, and typically 85% of the proteins in the coconut LPAAT S3 preparation are removed.

B. Hydroxylapatite Chromatography

Figure 7:
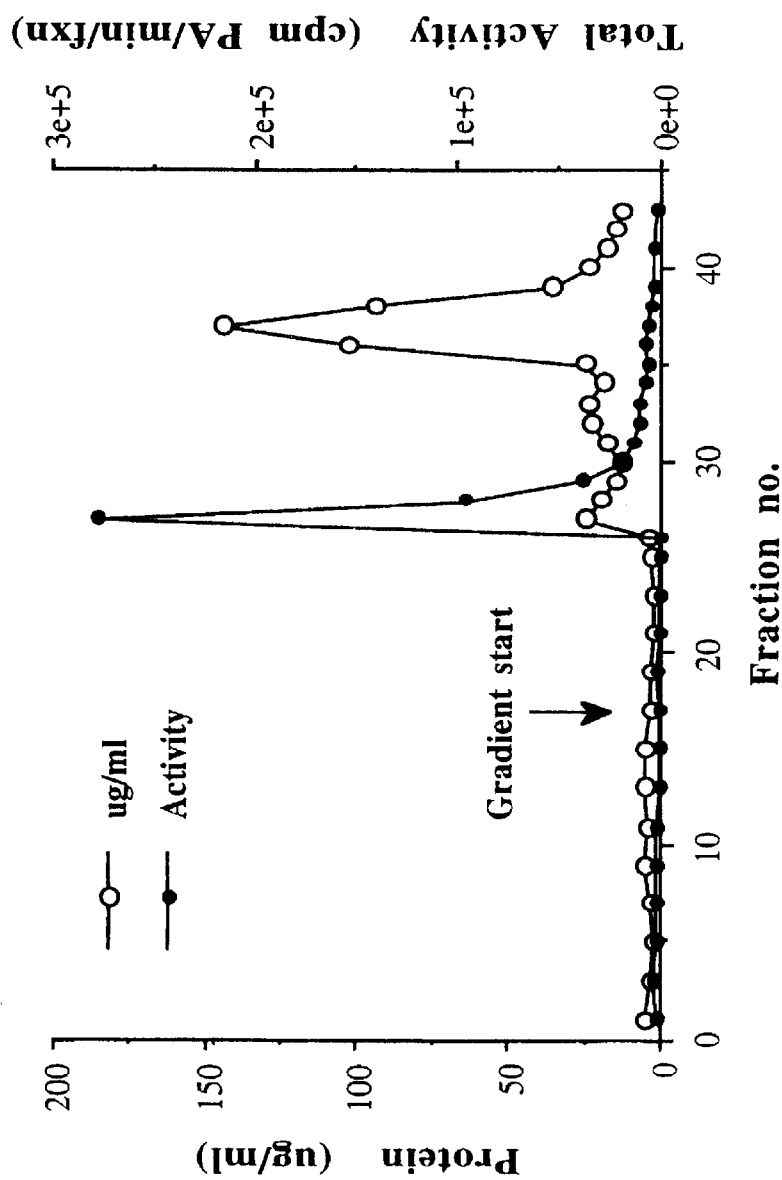
FIG. 7 shows the results of chromatography of coconut medium-chain LPAAT activity from the red 120 column on a column of hydroxyapatite.

The LPAAT-active fractions from the red column, in the buffer containing 2.5M NaCl, are pooled and applied to a 1.5 cm (diam.)×5.7 cm HA (hydroxylapatite) column 5 pre-equilibrated with running buffer containing 50 mM HEPES-NaOH, pH 7.5, 20% (w/v) glycerol, 1% (w/v) CHAPS, 1M NaCl, 5 mM β-ME. The flow rate is again 0.5 ml/min and fractions of 2 ml volume are collected. Essentially all of the protein and the LPAAT activity in the sample are bound by the column. The LPAAT activity and bound protein are substantially resolved by elution with a linear, 0–100 mM phosphate concentration gradient in the running buffer. These results are illustrated in FIG. 7.

The recovery of activity on this column is typically 60–70%. The LPAAT-active fractions are pooled and stored at −70° C. after freezing in liquid nitrogen. This active pool forms the starting material for additional purification experiments. Analysis of this preparation by size-exclusion chromatography shows that the LPAAT activity still behaves as though it were a globular protein of apparent molecular weight 44–50 kDa. This indicates that the partial purification through the red and HA columns does not result in any significant aggregation of the LPAAT with itself or with other proteins in the preparation, and does not compromise the solubilized state of the LPAAT protein.

In a typical application of this 2-column procedure, the final coconut LPAAT preparation contains 17% of the S1 activity and only 0.4% of the S1 protein. This represents a 40-fold purification of LPAAT relative to the S1 preparation.

Coconut LPAAT activity from the red+HA column sequence still prefers 12:0-CoA over 18:1-CoA as donor substrate, and will still utilize 12:0-LPA and 18:1-LPA as acceptor substrates. It still decreases as the assay NaCl concentration is raised above 200 mM, and tolerates freezing and thawing with minimal loss.

Example 6
Identification of Coconut LPAAT Protein

A. SDS PAGE Analysis of LPAAT from Hydroxylapatite Column

The protein composition of the LPAAT preparation obtained from the HA column is analyzed by SDS-PAGE. Visualization of the protein composition of P2, S3, or partially purified S3 preparations by SDS-PAGE requires that the sample not be boiled in the SDS-containing PAGE sample buffer prior to loading the gel. SDS-PAGE analysis reveals the presence of numerous protein species in the enriched LPAAT preparation. Although the protein composition is simplified relative to that of the S1 preparation, additional chromatography is required to identify the protein (or proteins) corresponding to LPAAT activity.

B. LPAAT Chromatography on 12:0-CoA Matrix

Useful resolution of the remaining proteins is obtained by chromatography on a matrix comprising immobilized 12:0-CoA substrate (unlabeled). The column matrix is prepared by attaching the amino group of the CoA moiety of 12:0-CoA to the free carboxyl group of 6-aminohexanoic acid Sepharose 4B. This Sepharose derivative, coupling procedure, and other necessary reagents are obtained from Sigma Chemical Company (St. Louis). A density of coupled 12:0-CoA of 3.9 mg/ml wet bead volume can be achieved. A 1 cm-diameter column is prepared with 2 ml of the 12:0-CoA matrix, and equilibrated with running buffer containing 50 mM HEPES-NaOH pH 7.5, 20% (w/v) glycerol, 1% (w/v) CHAPS, 0.4M NaCl, 5 mM β-ME at 0.2–0.5 ml/min.

Figure 8:
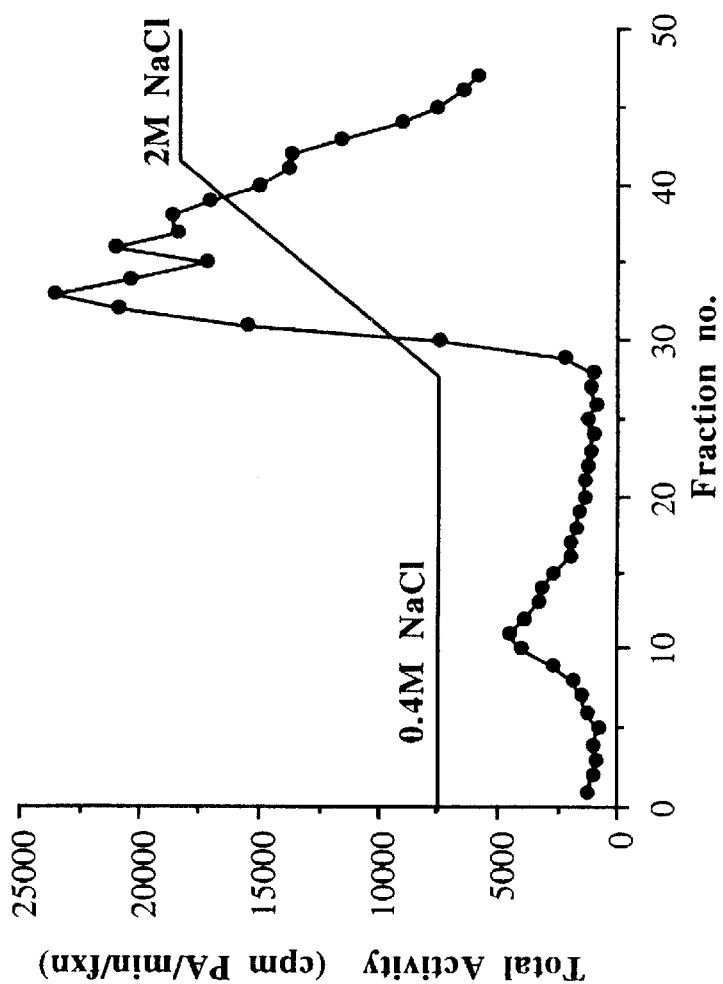
FIG. 8 shows the results of partially purified coconut medium-chain LPAAT preparation passed through a 12:0-CoA chromatography column.

The LPAAT preparation prepared by chromatography from the red and HA columns is diluted with running buffer lacking NaCl, lowering the NaCl concentration to 0.4M, and applied to the 12:0-CoA column. Fractions of 2 ml volume are collected. As shown in FIG. 8, a small amount of LPAAT activity emerges during the loading stage. However, the majority of the LPAAT activity is bound to the column and can be eluted later by application of a linear 0.4–2M NaCl gradient in the running buffer. Typically 50–60% of the loaded activity is recovered in this NaCl-eluted peak. If the experiment is repeated with the 6-aminohexanoic acid Sepharose 4B support lacking 12:0-CoA, most of the activity emerges in the loading effluent.

C. SDS PAGE Analysis of LPAAT from 12:0-CoA Column

Analysis of fractions eluted from the 12:0-CoA column by SDS-PAGE and silver-staining shows that considerable resolution of proteins is accomplished. Loading and washing fractions 7 and 10 (FIG. 8) contain a complex protein composition comparable to the sample loaded. Salt-eluted fractions 29–36 (FIG. 8) contain a much simpler protein composition as shown by two prominent component bands and 6–7 less abundant ones. Several very minor components are also detectable in this sample. The protein composition of such material varies somewhat from one coconut preparation to another, but the considerable purification obtained with the 12:0-CoA column is reproducible. Furthermore, on the SDS-polyacrylamide gel, a band or pair of bands corresponding to proteins having an approximate molecular weight of 27–29 kDa (i.e. migrating slightly faster in the gel than a marker protein of 31 kDa) is most prominent in intensity in fractions 32 and 33. These fractions also contain the maximum LPAAT activity. The 27–29 kDa band consistently tracks with LPAAT activity in the various coconut 12:0-CoA column samples examined. This is strong evidence that the 27–29 kDa protein (also referred to hereafter as the "29 kDa" protein or candidate protein) corresponds to the LPAAT enzyme. The other proteins in fractions 29–36 are most abundant in those fractions which are not at the peak of LPAAT activity, and are therefore less likely to represent LPAAT.

D. Chromatography of Activated LPAAT on 12:0-CoA Matrix

In a modification of the above 12:0-CoA chromatography method, LPAAT is activated with by addition of phospholipids prior to loading on the column. In addition, the running buffer is modified to include phospholipids. By these modifications, the LPAAT is maintained in activated form throughout the experiment.

To prepare modified running buffer, 380 μl of a detergent solution of phospholipids (50 mg/ml in 0.5% (w/v) CHAPS as described for the modified assay) are mixed with 9.5 ml of HA column running buffer and this mixture is then diluted by addition of 90 ml CHAPS-free buffer comprising 50 mM HEPES-NaOH, pH 7.5, 20% (w/v) glycerol, 0.44M NaCl, 5 mM β-ME. This results in final CHAPS and NaCl concentrations of 0.1% (w/v) and 0.5M respectively, and a phospholipid concentration as described for assay of solubilized LPAAT. Enzyme dilution buffer is prepared with phospholipids in the same manner, but such that the final CHAPS and NaCl concentrations are 0.1% (w/v) and 0.46M respectively. This dilution buffer is used to dilute the LPAAT sample from the HA column tenfold prior to loading on the 12:0-CoA column.

Figure 9:
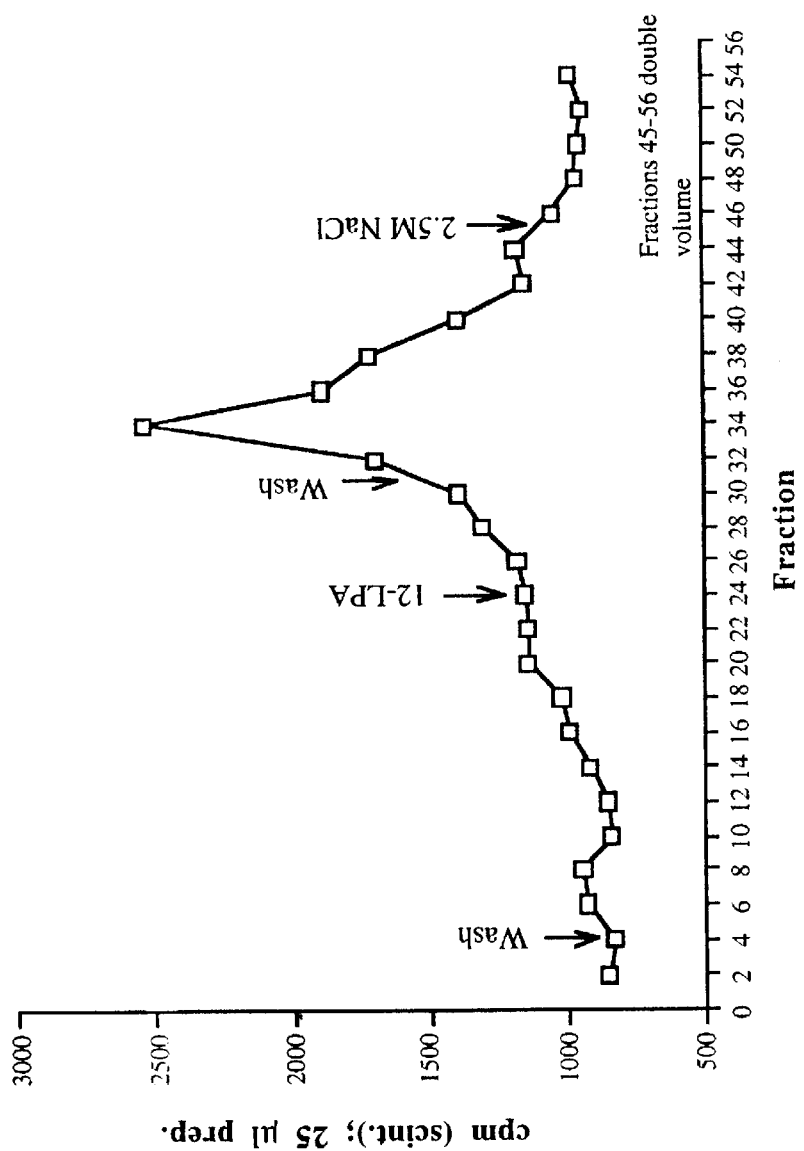
FIG. 9 provides the results of chromatography of partially purified, PL-activated coconut medium-chain LPAAT preparation on a 12:0-CoA column in the presence of phospholipids.

When applied in the presence of phospholipids only a small amount of LPAAT activity fails to be retained by the column. The activity may then be eluted at a slow rate as the column is washed with running buffer (FIG. 9). Application of 15 ml of 0.1 mM 12:0-LPA in the running buffer results in the elution of a single large peak of LPAAT activity. Subsequent application of 2.5M NaCl fails to elute additional detectable LPAAT.

Attempts to elute LPAAT from the 12:0-CoA column with 12:0-LPA or 18:1-LPA are unsuccessful (or provide only a very small peak of activity) unless the LPAAT is activated with phospholipids before loading and the column is run with phospholipid-containing buffer in the manner just described. This suggests that LPAAT binds differently to the column when it has been activated with phospholipids, and that this binding is based on recognition of the 12:0-CoA moiety of the column by the catalytic site of the LPAAT protein. The 12:0-LPA elution would then derive from recognition of the 12:0-LPA substrate by the LPAAT catalytic site also. These binding and elution phenomena, if based on the catalytic site, would be expected to be specific for LPAAT and to offer the prospect of considerable purification.

E. SDS PAGE Analysis of LPAAT from Activated 12:0-CoA Column

Examination of the eluted fractions by SDS-PAGE (with silver staining) shows that different proteins are present in the loading effluent, the LPAAT-active fractions, and the 2.5M NaCl effluent. The significantly stained 29 kDa LPAAT candidate protein is seen in the LPAAT-active fractions, along with several weakly staining protein bands. The 29 kDa protein is not detected in the LPAAT-inactive fractions. These results provide additional evidence that the 29 kDa protein represents coconut LPAAT.

F. Additional Chromatographic Analyses

Many other chromatography columns may be tested for their ability to resolve proteins present in active LPAAT preparations from the red+HA column sequence. Columns that are useful in this respect include Pharmacia "mono Q" anion exchanger, Merck thiophilic agarose, size exclusion columns, and blue 4 agarose. In all these chromatographic anslyses, LPAAT activity can be retained by the column and eluted in various ways, always accompanied by a protein or pair of proteins having an apparent molecular weight on SDS-PAGE of approximately 29 kDa.

Thus, the chromatographic evidence demonstrates the relationship between LPAAT activity and the protein or proteins migrating with apparent molecular weight of approximately 29 kDa on SDS-PAGE. Although this molecular weight does not correspond to the estimate of 44–50 kDa for the native enzyme obtained by size-exclusion chromatography, such differences between the molecular weights of denatured proteins on SDS-PAGE and the corresponding proteins in the native state are common. These differences can result from the association of the protein molecules into dimers, tetramers etc. in the native situation, or the binding of limited numbers of detergent molecules etc. during solubilization.

Example 7
Determination of LPAAT Amino Acid Sequence

A. Transfer of LPAAT to Membranes

LPAAT may be further purified for use in determination of amino acid sequence by transfer of the LPAAT preparation resulting from the Red 120 and HA column chromatography purification to nitrocellulose or PVDF membranes following SDS-PAGE. For example, for further use in tryptic digestions, the LPAAT protein is transferred to nitrocellulose. PVDF membranes, such as ProBlott (Applied Biosystems; Foster City, Calif.) and Immobilon-P (Millipore; Bedford, Mass.) find preferential use in different methods. For example, transfer to ProBlott is useful for N-terminal sequencing methods. For generation of peptides from cyanogen bromide digestion, Immobilon-P is preferred.

1. Blotting to Nitrocellulose

When protein is electroblotted to nitrocellulose, the blotting time is typically 1–5 hours in a buffer such as 25 mM Tris (tris(hydroxymethyl)aminomethane), 192 mM glycine in 5–20% methanol. Following electroblotting, membranes are stained in 0.1% (w/v) Ponceau S in 1% (v/v) acetic acid for 2 minutes and destained in 2–3 changes of 0.1% (v/v) acetic acid, 2 minutes for each change. These membranes are then stored wet in heat-sealed plastic bags at −20° C. If time permits, blots are not frozen but used immediately for digestion to create peptides for determination of amino acid sequence as described below.

2. Blotting to PVDF

When protein is electroblotted to Immobilon P PVDF, the blotting time is generally about 1–2 hours in a buffer such as 25 mM Tris/192 mM glycine in 20% (v/v) methanol. Following electroblotting to PVDF, membranes are stained in 0.1% (w/v) Coomassie Blue in 50% (v/v) methanol/10% (v/v) acetic acid for 5 minutes and destained in 2–3 changes of 50% (v/v) methanol/10% (v/v) acetic acid, 2 minutes for each change. PVDF membranes are then allowed to air dry for 30 minutes and are then stored dry in heat-sealed plastic bags at −20° C. Protein blotted to PVDF membranes such as Pro Blott, may be used directly to determine N-terminal sequence of the intact protein. A protocol for electroblotting proteins to ProBlott is described below.

B. Protease Digestion and Separation of Peptides

LPAAT protein that has been blotted to nitrocellulose may be subjected to digestion with proteases in order to obtain peptides for sequencing. The method used is that of Aebersold, et al. (*PNAS* (1987) 84:6970).

The LPAAT preparation is transferred to nitrocellulose as described above. The band representing the above-identified 29 kDa protein, and also an equal amount of blank nitrocellulose to be used as a control, are cut out of the nitrocellulose membrane. A 1.0 ml aliquot of 0.5% polyvinylpyrrolidone (PVP-40, Aldrich, Milwaukee, Wis.) in 100 mM acetic acid is added to the membrane pieces and the mixture incubated for 30 minutes at 37° C. In order to remove the PVP-40 completely, nitrocellulose pieces are washed with HPLC grade water (6×3 ml), checking the absorbance of the washes at 214 nm on a spectrophotometer. PVP-40 may be more easily removed if bands are not cut into small pieces until after PVP-40 treatment and washing.

Following the PVP-40 treatment, the membrane pieces are minced into small chips (~1 mm×1 mm) prior to digestion. The protein is then suspended in trypsin digest buffer (100 mM sodium bicarbonate pH 8.2). Acetonitrile is added to the digest mixture to a concentration of 5–10% (v/v). Trypsin is diluted in digest buffer and added to the digest mixture, at a ratio of 1:10 (w/w) protease to protein. Digests are incubated 18–24 hours at 37° C.

Following overnight incubation, the digest reaction is stopped by addition of 10 ml of 10% (v/v) trifluoroacetic acid (TFA) or 1 μl 100% TFA. The peptides in the digest mixture are separated on a Vydac reverse phase C18 column (2.1 mm×150 mm) installed in an Applied Biosystems (Foster City, Calif.) Model 130 High Performance Liquid Chromatograph (HPLC). Mobile phases used to elute peptides are: Buffer A: 0.1 mM sodium phosphate, pH2.2; Buffer B: 70% acetonitrile in 0.1 mM sodium phosphate, pH2.2. A 3-step gradient of 10–55% buffer B over two hours, 55–75% buffer B over 5 minutes, and 75% buffer B isocratic for 15 minutes at a flow rate of 50 ml/minute is used. Peptides are detected at 214 nm, collected by hand, and stored at −20° C.

Other proteases may also be used to digest the LPAAT protein in appropriate digest buffers, for example, endoproteinase gluC buffer (25 mM ammonium carbonate/1 mM EDTA, pH 7.8), or endoproteinase Asp-N buffer (0.05M sodium bicarbonate pH 8.0). In addition, buffer conditions, such as temperature may vary, for example endoproteinase gluC digestion is conducted at room temperature. However, the protocols for digestion, peptide separation and purification are substantially as described above for digestion with trypsin.

C. Cyanogen Bromide Cleavage and Segaration of Peptides

Cyanogen bromide cleavage may be performed on LPAAT protein using the methodology described in the Probe-Design Peptide Separation System Technical Manual from Promega, Inc. (Madison, Wis.). The LPAAT protein preparation is blotted to a PVDF membrane as described above. The portion of the membrane containing the transferred 29 kD band is cut from the blot, placed in a solution of cyanogen bromide in 70% (v/v) formic acid, and incubated overnight at room temperature. Following this incubation the cyanogen bromide solutions are removed, pooled and dried under a continuous nitrogen stream using a Reacti-Vap Evaporator (Pierce, Rockford, Ill.), or evaporated using a Speed-Vac. Additional elution of cyanogen bromide peptides from PVDF may be conducted to ensure complete removal, using a peptide elution solvent such as 70% (v/v) isopropanol, 0.2% (v/v) trifluoroacetic acid, 0.1 mM lysine, and 0.1 mM thioglycolic acid. The elution solvents are then removed and added to the tube containing the dried cyanogen bromide solution, and dried as described above. The elution procedure may be repeated with fresh elution solvent. 50 μl of HPLC grade water is then added to the dried peptides and the water removed by evaporation in a Speed-Vac (Savant, Inc., Farmingdale, N.Y.).

Peptides generated by cyanogen bromide cleavage are separated using a Tris/Tricine SDS-PAGE system similar to that described by Schagger and von Jagow (*Anal. Biochem.* (1987) 166:368–379). Gels are run at a constant voltage of 125–150 volts for approximately 1.5 hours or until the tracking dye has begun to run off the bottom edge of the gel. Gels may be pre-soaked in transfer buffer (125 mM Tris, 50 mM glycine, 10% (v/v) methanol) for 15–30 minutes prior to transfer. Gels are blotted to ProBlott sequencing membranes (Applied Biosystems, Foster City, Calif.) for 2 hours at a constant voltage of 50 volts. The membranes are stained with Coomassie blue (0.1% in 50% (v/v) methanol/10% (v/v) acetic acid) and destained for 3×2 min. in 50% (v/v) methanol/10% (v/v) acetic acid. Membranes are air-dried for 30–45 minutes before storing dry at −20° C.

Peptides blotted on to ProBlott can be directly loaded to the sequencer cartridge of the protein sequencer without the addition of a Polybrene-coated glass fibre filter. Peptides are sequenced using a slightly modified reaction cycle, BLOT-1, supplied by Applied Biosystems. Also, solution S3 (butyl chloride), is replaced by a 50:50 mix of S1 and S2 (n-heptane and ethyl acetate). These two modifications are used whenever samples blotted to ProBlott are sequenced.

D. N-terminal Secuencing of Proteins and Peptides

Sequencing is performed by Edman degradation on an Applied Biosystems 477A Pulsed-Liquid Phase Protein Sequencer; phenylthiohydantoin (PTH) amino acids produced by the sequencer are analyzed by an on-line Applied Biosystems 120A PTH Analyzer. Data are collected and stored using an Applied BioSystems model 610A data analysis system for the Apple Macintosh and also on to a Digital Microvax using ACCESS*CHROM software from PE NELSON, Inc. (Cupertino, Calif.). Sequence data is read from a chart recorder, which receives input from the PTH Analyzer, and is confirmed using quantitative data obtained from the model 610A software.

For peptide samples obtained as peaks off of an HPLC, the sample is loaded on to a Polybrene coated glass fiber filter (Applied Biosystems, Foster City, Calif.) which has been pre-washed. For peptides which have been reduced and alkylated, a portion of the PTH-amino acid product material from each sequencer cycle is counted in a liquid scintillation counter. For protein samples which have been electroblotted to Immobilon-P, the band of interest is cut out and then placed above a Polybrene coated glass fiber filter, prewashed as above and the reaction cartridge is assembled according to manufacturer's specifications. For protein samples which have been electroblotted to ProBlott, the glass fiber filter is not required.

In order to obtain protein sequences from small amounts of sample (5–30 pmoles), the 477A conversion cycle, the S4$_B$ solvent and the 120A analyzer program is modified as described by Tempst and Riviere (*Anal. Biochem.* (1989) 183:290).

Amino acid sequence of peptides generated from the 29 kDa LPAAT by trypsin digestion as described above are as follows:

| | |
|---|---|
| SQ1256 (SEQ ID NO: 1) | NLSLIIFPEGTr |
| SQ1262 (SEQ ID NO: 2) | YFSPIK |
| SQ1282 (SEQ ID NO: 3) | VRPAPITVK |

Amino acid sequence of peptides generated from the 29 kDa LPAAT by AspN digestion as described above are as follows:

| | |
|---|---|
| SQ1271 (SEQ ID NO: 4) | TGTHLa |
| SQ1272 (SEQ ID NO: 5) | VEMIHaly |
| SQ1276 (SEQ ID NO: 6) | slrvrpapitvk |
| SQ1281 (SEQ ID NO: 7) | FSPIKT |

The amino acid sequence is represented using the one letter code. Amino acids represented by lower case letters represent residues which were identified with a lesser degree of confidence.

E. Homology of LPAAT Peptide to Acyltransferase Proteins

The amino acid sequence of the LPAAT tryptic peptide SQ1256 described above is compared to known protein sequences in a computer data bank by computer aided homology search. Significant homology is found between the LPAAT peptide and the LPAAT encoded by the *E. coli* plsC gene. A six amino acid stretch of the 12 amino acid coconut LPAAT tryptic peptide is an identical match to amino acids 145–150 of the *E. coli* LPAAT (Coleman et al., supra). In addition, this same conserved six amino acid sequence is also found at amino acids 154–159 of a yeast acyltransferase protein encoded by the SLC1 gene. Additional regions of homology with the *E. coli* plsC and yeast SLC1 gene products are found in coconut LPAAT amino acid sequence as determined by translation of nucleic acid sequences of LPAAT PCR sequences described in Example 9.

Example 8
Preparation of Coconut CDNA Library

A. Total RNA Preparation

This procedure is an adaptation of the DNA isolation protocol of Webb and Knapp (D. M. Webb and S. J. Knapp, (1990) Plant Molec. Reporter, 8, 180–185). The following description assumes the use of 1 g fresh weight of tissue. Frozen immature endosperm tissue (from "green" coconuts as described for LPAAT purification) is powdered by grinding under liquid nitrogen. The powder is added to 10 ml REC buffer (50 mM Tris-HCl, pH 9, 0.8M NaCl, 10 mM EDTA, 0.5% w/v CTAB (cetyltrimethyl-ammonium bromide)) along with 0.2 g insoluble polyvinylpolypyrrolidone, and ground at room temperature. The homogenate is centrifuged for 5 minutes at 12,000× g to pellet insoluble material. The resulting supernatant fraction is filtered through Miracloth into a 3 ml phenol/chloroform preparation (phenol-saturated water/chloroform, 1/1 v/v, set to pH 7 with solid Tris base). After brief centrifugation as above to facilitate phase separation the upper phase is removed and the lower phase discarded. The upper phase is partitioned again with chloroform, and the top phase is again recovered.

The RNA is then precipitated by addition of 1 volume ethanol and collected by brief centrifugation as before. The RNA pellet is redissolved in 1 ml autoclaved 0.05% (w/v) DEPC (diethylpyrocarbonate), and reprecipitated by the addition of 1 ml 4M potassium acetate (pH 5), 0.05% (w/v) DEPC and incubation on ice for 2 hours. After collection by brief centrifugation, the RNA pellet is redissolved in 0.4 ml 0.05% (w/v) DEPC and extracted once more with phenol/chloroform as described above. Sufficient 3M potassium acetate (pH 5), 0.05% (w/v) DEPC is added to make the mixture 0.3M in acetate, followed by addition of two volumes of ethanol to precipitate the RNA. This final RNA precipitate is dissolved in 0.1 ml 0.05% (w/v) DEPC and stored frozen.

B. Construction of cDNA Library

A coconut endosperm cDNA library is constructed using Stratagene's (San Diego, Calif.) "UniZap" system, with the following modifications to the synthesis of first-strand cDNA. Forty $\mu$g of total RNA from coconut endosperm are reverse-transcribed in a 50 $\mu$l reaction volume as follows: The RNA, in $H_2O$, is heated at 65° C. for 20 minutes and chilled on ice. The first-strand synthesis is carried out as recommended by Stratagene, with the substitution of 600U "Superscript" reverse transcriptase, "Superscript" 1st-strand buffer, and DTT, all as supplied by BRL (Bethesda, Md.). The reaction mixture is incubated at 60° C. for 45 minutes. The remaining steps in the library synthesis are performed as recommended in the Stratagene "UniZap" protocol. The unamplified cDNA library obtained by this procedure contains 1.4×10$^6$ clones with an average insert size of 1.25 kb.

Example 9
Isolation of LPAAT-Encoding Sequences

DNA sequences encoding coconut LPAAT peptides are obtained using synthetic oligonucleotides designed from LPAAT peptide sequences. The LPAAT nucleic acid sequences may be obtained by amplification of DNA by polymerase chain reaction (PCR) using the oligonucleotides as primers, or alternatively, by screening a cDNA or genomic DNA library by radiolabeling the oligonucleotides for use as probes.

A. Synthetic Oligonucleotides

For use as PCR primers from single stranded DNA template reverse-transcribed from mRNA, oligonucleotides containing the sense orientation sequence corresponding to LPAAT peptide encoding sequences are prepared. These oligonucleotides are used as primers for the "forward" amplification reaction to produce sense strand DNA.

For the "reverse" reaction for amplification of the non-coding DNA strand, an oligonucleotide may be designed to be identical to a portion of a primer used to prepare DNA template for PCR. Alternatively, oligonucleotides which contain sequence complementary to LPAAT peptide encoding sequences may be used in combination with a "forward" LPAAT oligonucleotide primer as described above.

Where the LPAAT peptide sequences contain amino acids which may be encoded by a number of different codons, the forward or reverse primers may be "degenerate" oligonucleotides, i.e. containing a mixture of all or some of the possible encoding sequences for a particular peptide region. To reduce the number of different oligonucleotides present in such a mixture, it is preferable to select peptide regions which have the least number of possible encoding sequences when preparing the synthetic oligonucleotide for PCR primers. Similarly, where the synthetic oligonucleotide is to be used to directly screen a library for LPAAT sequences, lower degeneracy oligonucleotides are preferred.

In addition to LPAAT encoding sequence, oligonucleotides for primers in PCR will contain additional, non-LPAAT, sequences to aid in cloning of the PCR products into convenient plasmid vectors. The non-LPAAT sequences may be for restriction digestion sites which may be used to clone the PCR fragments into various plasmids, or may be designed to contain sequences useful for cloning into a particular commercially available vector. For example, the synthetic oligonucleotides described below contain sequences useful for cloning using the CLONEAMP™ system (GIBCO BRL; Gaithersburg, Md.), which utilizes UDG (uracil DNA glycosylase) for directional cloning of PCR products (Nisson et al. (1991) *PCR Meth. and Appl.* 1:120–123).

Following are sequences of synthetic oligonucleotides which may be used to obtain LPAAT sequences. The oligonucleotide names reflect the particular LPAAT peptide fragment numbers as listed in Table 1. The letter "F" in the oligonucleotide name designates a PCR forward reaction primer. The letter "R" designates a PCR reverse reaction primer. The letter "P" designates an oligonucleotide to be radiolabeled for use as a probe in cDNA or genomic library screening. The underlined portion of the PCR primers indicates the LPAAT peptide encoding sequence.

The nucleotide base codes for the above oligonucleotides are as follows:

A=adenine T=thymine Y=cytosine or thymine
C=cytosine U=uracil R=adenine or guanine
G=guanine I=inosine O=inosine or cytosine
H=adenine, cytosine or thymine
N=adenine, cytosine, guanine or thymine B. PCR Reactions Poly(A)+ RNA is isolated from total RNA prepared from coconut endosperm tissue as described in Example 8. Single-stranded cDNA is prepared from coconut poly(A)+ or total RNA by reverse transcription using Superscript reverse transcriptase (BRL) and TSYN as the oligonucleotide primer. The reaction is conducted according to manufacturer's directions, except that the reaction is run at 45° C. rather than 37° C.

PCR is conducted in a Perkin Elmer Cetus GeneAmp PCR System 9600 PCR machine using reverse transcribed single-stranded coconut embryo cDNA as template. Commercially available PCR reaction and optimization reagents

```
SQ1256-1  5' CUACUACUACUAAATHATHTTYCCOGARGG 3' (SEQ ID NO:8)

SQ1256-R1 5' CAUCAUCAUCAUCCYTCGGRAAIATIAT 3' (SEQ ID NO:9)

SQ1262-F1 5' CUACUACUACUATAYTTYWSOCCOATHAA 3' (SEQ ID NO:10)

SQ1262-R1 5' CAUCAUCAUCAUYTTDATOGGOSWRAARTA 3' (SEQ ID NO:11)

SQ1272-F1 5' CUACUACUACUAGTOGARATGATHCA 3' (SEQ ID NO:12)

SQ1272-R1 5' CAUCAUCAUCAURTGDATCATYTCOAC 3' (SEQ ID NO:13)

SQ1272-P1 5' RTGDATCATYTCOAC 3' (SEQ ID NO:14)

SQ1272-P2 5' RTGDATCATYTCNAC 3' (SEQ ID NO:15)
```

An oligonucleotide, TSYN, is used for reverse transcription from poly(A)+ or total RNA to prepare single-stranded DNA for use as a PCR template. In addition to a poly(T) region for binding to the mRNA poly(A) tail, the oligonucleotide contains restriction digestion sequences for HindIII, PstI and SstI. The sequence of TSYN is as follows:

are used according to manufacturer's specifications. The following reactions using the above described synthetic oligonucleotides are run:

```
TSYN 5' CCAAGCTTCTGCAGGAGCTCTTTTTTTTTTTTTT 3' (SEQ ID NO:16)
```

An oligonucleotide, 5' RACEAMP, is useful in the reverse reaction of PCR for amplification of the antisense strand of an LPAAT encoding sequence. It is noted that where the template for PCR is single stranded DNA reverse-transcribed from mRNA, the reverse reaction will not occur until completion of the first forward reaction. The first strand reaction results in production of a sense strand template which may then be used in amplification of the antisense DNA strand from the reverse primer. In addition to a region of identity with TSYN (restriction digest region), 5'RACEAMP contains the 5° CAU stretch used in the CLONEAMP™ cloning system. The sequence of 5'RACEAMP is as follows:

| Reaction | Forward Primer | Reverse Primer |
|---|---|---|
| 1 | SQ1256-1 | 5'RACEAMP |
| 2 | SQ1262-F1 | 5'RACEAMP |
| 3 | SQ1272-F1 | 5'RACEAMP |
| 4 | SQ1262-F1 | SQ1256-R1 |
| 5 | SQ1262-F1 | SQ1272-R1 |
| 6 | SQ1256-1 | SQ1262-R1 |
| 7 | SQ1256-1 | SQ1272-R1 |
| 8 | SQ1272-F1 | SQ1256-R1 |
| 9 | SQ1272-F1 | SQ1262-R1 |

```
5'RACEAMP 5' CAUCAUCAUCAUAAGCTTCTGCAGGAGCTC 3' (SEQ ID NO:17)
```

DNA fragments generated in PCR reactions are cloned into pAMP1 (CLONEAMP™ system; GIBCO BRL). The DNA sequence of the cloned fragments are determined to confirm that the cloned fragments encode LPAAT peptides.

Sequence of two PCR products, 23-2 and 23-4, from reaction 7, and one PCR product, 10-1, from reaction 6, are confirmed as encoding LPAAT peptides by DNA sequence and translated amino acid sequence analysis. The sequences of these reactions are provided in FIGS. 10–12.

In FIG. 10, DNA and translated amino acid sequences of clone 23-2, obtained by PCR with oligonucleotides SQ1256-1 and SQ1272-R1, are shown. Translation of the DNA sequence in portions of two different reading frames is required to locate the expected LPAAT peptide regions encoded in the PCR primers. Translated sequence of nucleotides 13–30 corresponds to amino acids 5–10 of the tryptic peptide SQ1256 (SEQ ID NO:1), which were encoded by the forward primer. Nucleotides 245–259 correspond to amino acids 1–5 of the AspN peptide SQ1272 (SEQ ID NO:5), encoded by the reverse primer. Translation of nucleotides 32–259 corresponds to additional LPAAT peptide sequences. For example, nucleotides 32–37 encode amino acids 11–12 of SQ1256, although in a different translation frame from the sequence encoding amino acids 5–10 of SQ1256. From this information, as well as by comparison to sequence of clone 23-4 (FIG. 11), it appears that an additional nucleotide not present in LPAAT encoding sequence was incorporated into the LPAAT encoding sequence (most likely an extra guanine in nucleotides 27–30) during the polymerase chain reaction.

In addition to the expected LPAAT amino acid sequences from the forward and reverse primers, the 23-2 translated sequence corresponds to other LPAAT peptide sequences. Nucleotides 125–142 encode the AspN peptide SQ1271 (SEQ ID NO:4); nucleotides 155–190 encode the AspN peptide SQ1276 (SEQ ID NO:6), as well as tryptic peptide SQ1282 (SEQ ID NO:3) (SQ1282 is identical to amino acids 4–12 of SQ1276); and nucleotides 191–211 encode the AspN peptide SQ1281 (SEQ ID NO:7) and tryptic peptide SQ1262 (SQ ID NO:2).

DNA sequence of a second clone, 23-4, of a larger reaction 7 PCR product is shown in FIG. 11. In this sequence, the last two amino acids of the SQ1256 peptide are encoded in frame with amino acids 5–10 (encoded by the PCR primer). The difference in size between the 23-4 insert (approximately 360 bp) and the 23-2 product (approximately 270 bp) is apparently due to the presence of an unprocessed intron in the 23-4 sequence (untranslated sequence at nucleotides 70–157 of FIG. 11). The presence of the intron is likely due to an unprocessed LPAAT RNA in the total RNA (as opposed to poly(A)+) used to generate the single-stranded cDNA PCR template.

Excluding the intron and PCR primer regions, the LPAAT sequences of the inserts in 23-2 and 23-4 match at all but a single nucleotide, namely nucleotide 90 of 23-2, which is a thymine, and corresponding nucleotide 177 of 23-4, which is a cytosine. This nucleotide difference also results in a difference in the translated amino acid sequence of 23-2 and 23-4. A leucine is encoded by nucleotides 89–91 in 23-2, and a proline is encoded by corresponding nucleotides 176–178 of 23-4.

DNA sequence of the approximately 220 bp insert in the cloned PCR product of reaction 6, 10-1, is provided in FIG. 12. The LPAAT encoding sequence of this clone, with the exception of the PCR primer regions, is identical to that of 23-4 in the shared region.

C. Library Screening

1. Synthetic Oligonucleotide as Probe

Useful hybridization solutions for library screening with oligonucleotide probes, such as SQ1272-P1 or SQ1272-P2, include tetraalkylammonium salt solutions, such as described by Jacobs, et al. (*Nucl. Acids Res.* (1988) 16:4637–4650). Appropriate hybridization conditions, such as hybridization and washing temperatures, may also be determined by Northern analysis of RNA blots containing RNA from the enzyme source, ie. coconut endosperm. The oligonucleotide may then be radiolabeled and hybridized with clones from the coconut cDNA library described above, or from a coconut genomic library, in order to identify clones containing sequences encoding LPAAT peptides.

2. PCR Product as Probe

LPAAT DNA fragments obtained by PCR as described above may also be radiolabeled and used as probes for coconut LPAAT clones (Maniatis, supra). An approximately 280 bp fragment of clone 23-2 containing the LPAAT encoding region is obtained by digestion of 23-2 with XbaI and SalI and isolation of the resulting approximately 280 bp fragment. The fragment is radiolabeled by random priming using a random labeling kit (Stratagene; La Jolla, Calif.). Approximately 240,000 plaques of the coconut endosperm cDNA library in the UniZap phage are plated, lifted onto nylon membrane filters and hybridized to the labeled LPAAT 23-2 fragment. Hybridization is conducted at 42° C. in hybridization solution containing 50% formamide, 5× SSC (1× SSC=0.15 M NaCl; 0.015 M Na citrate), 0.1% SDS, 0.1 mg/ml salmon sperm DNA, 10× Denhardt's solution. The filters are washed in 1× SSC, 0.1% SDS at room temperature for 30 minutes, followed by two 30 minute washes in the same solution at 37° C. A total of 32 hybridizing plaques are identified. The identified plaques are replated and hybridization with the radiolabeled plaque is repeated to obtain purified cultures of the LPAAT containing phage. The LPAAT cDNA fragments are excised from the UniZap phage vector according to manufacturer's (Stratagene) directions. Briefly, a helper phage system is used which results in automatic excision and recircularization of excised cDNA to generate subclones in a pBluescript SK- (Stratagene) phagemid vector. The LPAAT subclones are further analyzed by PCR to determine the lengths of the various inserts and 3' non-coding sequences are obtained and analyzed to determine the number of classes of LPAAT clones. The longest clones from each class are analyzed to determine DNA sequence of coconut LPAAT.

Example 10

Constructs for Plant Transformation

DNA constructs for use in plant transformation are prepared. For uses in expression in plant oilseed crops for modification of TAG, LPAAT encoding sequences may be inserted into expression cassettes containing regulatory regions which provide for preferential expression in plant seed tissues. Examples of genes from which such expression cassettes may be prepared include seed ACP, a Bce4 gene from Brassica seeds, and a Brassica napin gene. See, for example, Kridl et al. (in *Control of Plant Gene Expression* (1993) Chapter 30, pages 481–498, ed. D. P. S. Verma, CRC Press) for a discussion expression cassettes for use in expression of genes in plant seed tissues.

Constructs for plant transformation are prepared by transfer of the expression cassettes containing LPAAT sequences into convenient cloning sites on a binary vector such as those described by McBride et al. (supra). The binary constructs are then transformed into cells of an appropriate Agrobacterium strain, such as EHA101 (Hood et al. (1986) *J. Bacteriol.* 168:1291–1301) as per the method of Holsters et al. (*Mol. Gen. Genet.* (1978) 163:181–187) for use in preparation of transgenic plants.

Example 11
Transformation with LPAAT Constructs

A variety of methods have been developed to insert a DNA sequence of interest into the genome of a plant host to obtain the transcription or transcription and translation of the sequence to effect phenotypic changes.

Transgenic Brassica plants are obtained by Agrobacterium-mediated transformation as described by Radke et al. (*Theor. Appl. Genet.* (1988) 75:685–694; *Plant Cell Reports* (1992) 11:499–505). Transgenic *Arabidopsis thaliana* plants may be obtained by Agrobacterium-mediated transformation as described by Valverkens et al., (*Proc. Nat. Acad. Sci.* (1988) 85:5536–5540). Other plant species may be similarly transformed using related techniques.

Alternatively, microprojectile bombardment methods, such as described by Klein et al. (*Bio/Technology* 10:286–291) may also be used to obtain nuclear transformed plants comprising the viral single subunit RNA polymerase expression constructs described herein.

Example 12
Triacylglyceride Analysis

The fatty acid compositions of different lipid classes extracted from mature seeds can be examined by the following method. Analyses of the acyl compositions of the sn-2 and sn-1+3 positions of TAG are conducted using the pancreatic lipase protocol (Brockerhoff (1975), supra). Ideally with this protocol, the lipase cleaves fatty acids from the sn-1 and sn-3 positions, and not from the sn-2 position. Thus, the fatty acids in the resulting mono-glyceride are presumed to be those in the sn-2 position. However, it is noted that those previously attempting to study TAG having shorter-chain fatty acids by this method (Entressangles et al. (1964) *Biochim. Biophys. Acta* 84:140–148), reported that shorter-chain fatty acids located at the sn-2 position were quickly hydrolyzed during such a digestion, which the authors reported to be the result of a spontaneous migration of internal shorter-chain fatty acids towards outer positions in diglycerides and monoglycerides.

Oil distilled from mature seeds may be subjected to a pancreatic lipase digestion protocol modified from Brockerhoff et al., supra, to minimize acyl migration. This distinguishes acyl compositions of the sn-2 and sn-1+3 combined positions. The modifications are as follows: pH is lowered to neutrality, reaction time is shortened from 15 to 3 minutes, samples are maintained at acidic pH thereafter, and digestion products are chromatographed on borate-impregnated TLC plants. The chromatographed products are then eluted and analyzed as fatty acid methyl esters as before.

By the above examples, solubilization and properties of LPAAT activity from plant seed tissues is described. A protocol is provided to obtain substantially purified medium-chain acyl-CoA-preferring LPAAT from coconut endosperm. Various properties of the protein are described, including methods to obtain and use amino acid and nucleic acid sequence related thereto. Nucleic acid sequences obtained in this manner are provided, and their use in isolation of plant LPAAT genes is described. Thus, through this invention, one can obtain the amino acid and nucleic acid sequences which encode LPAATs from a variety of sources and for a variety of applications. These LPAAT sequences may then be expressed in transgenic plants to obtain altered triacylglycerides as described.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. A DNA construct comprising a first DNA sequence encoding a coconut plant 1-acylglycerol-3-phosphate acyltransferase peptide joined to a second DNA sequence heterologous to said first DNA sequence, wherein said first DNA sequence is obtainable by:

(i) contacting, under polymerase chain reaction conditions, (a) an oligonucleotide primer encoding six contiguous amino acids of the peptide represented as SEQ ID NO: 1 (b) DNA from a coconut plant 1-acylglycerol-3-phosphate acyltransferase source and (c) a second oligonucleotide primer;

(ii) recovering a DNA sequence which encodes a plant 1-acylglycerol-3-phosphate acyltransferase peptide.

2. The DNA construct of claim 1 wherein said DNA from a coconut 1-acylglycerol-3-phosphate acyltransferase source is single-stranded cDNA.

3. The DNA construct of claim 1 wherein said 1-acylglycerol-3-phosphate acyltransferase source is immature endosperm.

4. A DNA sequence encoding a coconut 1-acylglycerol-3-phosphate acyltransferase obtained by probing a cDNA or genomic DNA library isolated from a plant 1-acylglycerol-3-phosphate acyltransferase source with said first DNA sequence of claim 1.

5. A DNA construct comprising a naturally derived sequence from a plant 1-acylglycerol-3-phosphate acyltransferase gene, wherein said DNA construct further comprises a DNA sequence not naturally associated with said acyltransferase sequence, and wherein said plant DNA acyltransferase sequence comprises an approximately 200 base pair encoding region which will hybridize with the 1-acylglycerol-3-phosphate acyltransferase protein encoding sequence shown in any one of FIGS. 10–12 (SEQ ID NOS:18–20) when said hybridization is conducted at 42° C. in a solution comprising 50% formamide and 5× SSC.

6. The construct of claim 5, wherein said acyltransferase encoding sequence is from a plant seed source.

7. The construct of claim 5, wherein said plant is coconut.

8. A DNA construct according to claim 5 wherein said construct comprises:

a transcriptional initiation region functional in a host cell operatively joined 5' to said sequence from a plant 1-acylglycerol-3-phosphate acyltransferase gene.

9. The construct of claim 8, wherein said host cell is a plant cell.

10. The construct according to claim 9, wherein said transcriptional initiation region is from a gene preferentially expressed in plant seed tissue.

11. A cell comprising a construct according to claim 8.

12. A plant cell comprising a construct according to claim 9.

13. The DNA construct of claim 1 wherein said second oligonucleotide primer corresponds to sequence of the encoding region for at least six contiguous amino acids of a coconut 1-acylglycerol-3-phosphate acyltransferase peptide.

14. The DNA construct of claim 1 wherein said DNA from a coconut 1-acylglycerol-3-phosphate acyltransferase source is present on a cloning vector, and said second oligonucleotide primer comprises a region corresponding with sequence in said cloning vector.

15. A DNA construct comprising a sequence encoding a coconut 1-acylglycerol-3-phosphate acyltransferase protein, wherein said construct further comprises a DNA sequence not naturally associated with said acyltransferase encoding sequence.

16. The DNA construct of claim 15 wherein said coconut acyltransferase encoding sequence is obtained by screening a coconut gene library with a portion of a coconut 1-acylglycerol-3-phosphate acyltransferase protein encoding sequence obtained by PCR, wherein said PCR is conducted using an oligonucleotide primer encoding 5 consecutive amino acids of a coconut 1-acylglycerol-3-phosphate acyltransferase protein sequence shown in FIGS. 10–12 (SEQ ID NOS:18–20) and a second oligonucleotide primer.

17. The DNA construct of claim 15 wherein said coconut 1-acylglycerol-3-phosphate acyltransferase protein has preferential activity on medium-chain acyl-CoA donor substrates.

18. A DNA construct according to claim 15 wherein said construct further comprises:
a transcriptional initiation region functional in a host cell operatively joined 5' to said sequence encoding a coconut 1-acylglycerol-3-phosphate acyltransferase protein.

19. The construct of claim 18, wherein said host cell is a plant cell.

20. The construct according to claim 19, wherein said transcriptional initiation region is from a gene preferentially expressed in plant seed tissue.

21. A cell comprising a construct according to claim 18.

22. A plant cell comprising a construct according to claim 19.

23. The DNA construct of claim 1 wherein said first DNA sequence encodes the 1-acylglycerol-3-phosphate acyltransferase peptide sequence shown in any one of FIGS. 18–20 (SEQ ID NOS:18–20).

24. The DNA construct of claim 15 wherein said construct comprises sequence encoding the 1-acylglycerol-3-phosphate acyltransferase peptide sequence shown in any one of FIGS. 18–20 (SEQ ID NOS:18–20).

25. The DNA construct of claim 1 wherein said first DNA sequence comprises the 1-acylglycerol-3-phosphate acyltransferase peptide encoding sequence shown in any one of FIGS. 18–20 (SEQ ID NOS:18–20).

26. The DNA construct of claim 15 wherein said construct comprises the 1-acylglycerol-3-phosphate acyltransferase encoding sequence shown in any one of FIGS. 18–20 (SEQ ID NOS:18–20).

* * * * *

SEQUENCE LISTING (1) GENERAL INFORMATION:

(iii) NUMBER OF SEQUENCES: 20

(2) INFORMATION FOR SEQ ID NO: 1:

(i) SEQUENCE CHARACTERISTICS:
      (A) LENGTH:  12 amino acids
      (B) TYPE:    amino acid
      (D) TOPOLOGY: linear (ii) MOLECULE TYPE:   peptide (xi) SEQUENCE DESCRIPTION: SEQ ID NO:1:

Asn Leu Ser Leu Ile Ile Phe Pro Glu Gly Thr Arg
               5                   10

(2) INFORMATION FOR SEQ ID NO: 2:

(i) SEQUENCE CHARACTERISTICS:
      (A) LENGTH:   6 amino acids

```
        (B) TYPE:  amino acid
        (D) TOPOLOGY: linear (ii) MOLECULE TYPE:  peptide (xi) SEQUENCE DESCRIPTION: SEQ ID NO: 2:

Tyr Phe Ser Pro Ile Lys
              5

(2) INFORMATION FOR SEQ ID NO: 3:

(i) SEQUENCE CHARACTERISTICS:
        (A) LENGTH:  9 amino acids
        (B) TYPE:  amino acid
        (D) TOPOLOGY: linear (ii) MOLECULE TYPE:  peptide (xi) SEQUENCE DESCRIPTION: SEQ ID NO: 3:

Val Arg Pro Ala Pro Ile Thr Val Lys
              5

(2) INFORMATION FOR SEQ ID NO: 4:

(i) SEQUENCE CHARACTERISTICS:
        (A) LENGTH:  6 amino acids
        (B) TYPE:  amino acid
        (D) TOPOLOGY: linear (ii) MOLECULE TYPE:  peptide (xi) SEQUENCE DESCRIPTION: SEQ ID NO: 4:

Thr Gly Thr His Leu Ala
              5

(2) INFORMATION FOR SEQ ID NO: 5:

(i) SEQUENCE CHARACTERISTICS:
        (A) LENGTH:  8 amino acids
        (B) TYPE:  amino acid
        (D) TOPOLOGY: linear (ii) MOLECULE TYPE:   peptide (xi) SEQUENCE DESCRIPTION: SEQ ID NO: 5:

Val Glu Met Ile His Ala Leu Tyr
              5

(2) INFORMATION FOR SEQ ID NO: 6:

(i) SEQUENCE CHARACTERISTICS:
        (A) LENGTH:  12 amino acids
        (B) TYPE:  amino acid
        (D) TOPOLOGY: linear (ii) MOLECULE TYPE:  peptide (xi) SEQUENCE DESCRIPTION: SEQ ID NO: 6:

Ser Leu Arg Val Arg Pro Ala Pro Ile Thr Val Lys
              5                  10

(2) INFORMATION FOR SEQ ID NO: 7:

(i) SEQUENCE CHARACTERISTICS:
        (A) LENGTH:  6 amino acids
        (B) TYPE:  amino acid
        (D) TOPOLOGY: linear (ii) MOLECULE TYPE:   peptide
```

(xi) SEQUENCE DESCRIPTION: SEQ ID NO: 7:

Phe Ser Pro Ile Lys Thr
                    5

(2) INFORMATION FOR SEQ ID NO: 8:

(i) SEQUENCE CHARACTERISTICS:
        (A) LENGTH: 29 base pairs
        (B) TYPE:   nucleic acid
        (C) STRANDEDNESS: single
        (D) TOPOLOGY:  linear (ii) MOLECULE TYPE:   other
        (A) DESCRIPTION:    synthetic oligonucleotide (ix) FEATURE: N at 24 = inosine or cytosine (xi) SEQUENCE DESCRIPTION: SEQ ID NO: 8:

CUACUACUAC UAATHATHTT YCCNGARGG                              29

(2) INFORMATION FOR SEQ ID NO: 9:

(i) SEQUENCE CHARACTERISTICS:
        (A) LENGTH:  29 base pairs
        (B) TYPE:   nucleic acid
        (C) STRANDEDNESS:   single
        (D) TOPOLOGY:   linear (ii) MOLECULE TYPE:   other
        (A) DESCRIPTION:    synthetic oligonucleotide (ix) FEATURE:         N at 18 = inosine or cytosine
            N at 24 = inosine
            N at 27 = inosine (xi) SEQUENCE DESCRIPTION: SEQ ID NO: 9:

CAUCAUCAUC AUCCYTCNGG RAANATNAT                              29

(2) INFORMATION FOR SEQ ID NO: 10:

(i) SEQUENCE CHARACTERISTICS:
        (A) LENGTH:  29  base pairs
        (B) TYPE:  nucleic acid
        (C) STRANDEDNESS: single
        (D) TOPOLOGY:   linear (ii) MOLECULE TYPE:   other
        (A) DESCRIPTION:    synthetic oligonucleotide (ix) FEATURE:         N at 21 = inosine or cytosine
            N at 24 =  inosine or cytosine (xi) SEQUENCE DESCRIPTION: SEQ ID NO: 10:

CUACUACUAC UATAYTTYWS NCCNATHAA                              29

(2) INFORMATION FOR SEQ ID NO: 11:

(i) SEQUENCE CHARACTERISTICS:
        (A) LENGTH: 30 base pairs
        (B) TYPE:   nucleic acid
        (C) STRANDEDNESS: single
        (D) TOPOLOGY:   linear (ii) MOLECULE TYPE:   other
        (A) DESCRIPTION:    synthetic oligonucleotide (ix) FEATURE:         N at 19 = inosine or cytosine
            N at 22 = inosine or cytosine (xi) SEQUENCE DESCRIPTION: SEQ ID NO: 11:

```
CAUCAUCAUC AUYTTDATNG GNSWRAARTA                                    30

(2) INFORMATION FOR SEQ ID NO: 12:

(i) SEQUENCE CHARACTERISTICS:
         (A) LENGTH: 26 base pairs
         (B) TYPE:   nucleic acid
         (C) STRANDEDNESS: single
         (D) TOPOLOGY:   linear (ii) MOLECULE TYPE: other
         (A) DESCRIPTION:     synthetic oligonucleotide (ix) FEATURE:         N at 15 =  inosine or cytosine (xi) SEQUENCE DESCRIPTION: SEQ ID NO: 12:

CUACUACUAC UAGTNGARAT GATHCA                                        26

(2) INFORMATION FOR SEQ ID NO: 13:

(i) SEQUENCE CHARACTERISTICS:
         (A) LENGTH: 27 base pairs
         (B) TYPE:   nucleic acid
         (C) STRANDEDNESS:  single
         (D) TOPOLOGY:   linear (ii) MOLECULE TYPE:  other
         (A) DESCRIPTION:     synthetic oligonucleotide (ix) FEATURE:         N at 25 =  inosine or cytosine (xi) SEQUENCE DESCRIPTION: SEQ ID NO: 13:

CAUCAUCAUC AURTGDATCA TYTCNAC                                       27

(2) INFORMATION FOR SEQ ID NO: 14:

(i) SEQUENCE CHARACTERISTICS:
         (A) LENGTH: 15 base pairs
         (B) TYPE:   nucleic acid
         (C) STRANDEDNESS: single
         (D) TOPOLOGY: linear (ii) MOLECULE TYPE:   other
         (A) DESCRIPTION:     synthetic oligonucleotide (ix) FEATURE:         N at 13 =  inosine or cytosine (xi) SEQUENCE DESCRIPTION: SEQ ID NO: 14:

RTGDATCATY TCNAC                                                    15

(2) INFORMATION FOR SEQ ID NO: 15:

(i) SEQUENCE CHARACTERISTICS:
         (A) LENGTH: 15 base pairs
         (B) TYPE:   nucleic acid
         (C) STRANDEDNESS: single
         (D) TOPOLOGY:   linear (ii) MOLECULE TYPE:   other
         (A) DESCRIPTION:     synthetic oligonucleotide (ix) FEATURE:         N at 13 =  adenine, cytosine, guanine or (xi) SEQUENCE DESCRIPTION: SEQ ID NO: 15:

RTGDATCATY TCNAC                                                    15

(2) INFORMATION FOR SEQ ID NO: 16:

(i) SEQUENCE CHARACTERISTICS:
```

```
        (A) LENGTH: 35 base pairs
        (B) TYPE:   nucleic acid
        (C) STRANDEDNESS: single
        (D) TOPOLOGY:    linear (ii) MOLECULE TYPE:  other
        (A) DESCRIPTION:   synthetic oligonucleotide (xi) SEQUENCE DESCRIPTION: SEQ ID NO: 16:

CCAAGCTTCT GCAGGAGCTC TTTTTTTTTT TTTTT                                35

(2) INFORMATION FOR SEQ ID NO: 17:

(i) SEQUENCE CHARACTERISTICS:
        (A) LENGTH: 30 base pairs
        (B) TYPE:   nucleic acid
        (C) STRANDEDNESS: single
        (D) TOPOLOGY:    linear (ii) MOLECULE TYPE:  other
        (A) DESCRIPTION:   synthetic oligonucleotide (xi) SEQUENCE DESCRIPTION: SEQ ID NO: 17:

CAUCAUCAUC AUAAGCTTCT GCAGGAGCTC                                      30

(2) INFORMATION FOR SEQ ID NO: 18:

(i) SEQUENCE CHARACTERISTICS:
        (A) LENGTH: 271 base pairs
        (B) TYPE:   nucleic acid
        (C) STRANDEDNESS: single
        (D) TOPOLOGY:    linear (ii) MOLECULE TYPE:   cDNA to mRNA (xi) SEQUENCE DESCRIPTION: SEQ ID NO: 18:

CTACTACTAC TA ATA ATA TTT CCG GAG GGG T ACT CGA TCG AAA ACA GGA        49
            Ile Ile Phe Pro Glu Gly   Thr Arg Ser Lys Thr Gly

AGG CTG CTT CCA TTT AAG AAG GGT TTT ATT CAC ATA GCA CTT CAG ACA        97
Arg Leu Leu Pro Phe Lys Lys Gly Phe Ile His Ile Ala Leu Gln Thr

CGG TTG CCG ATA GTT CCA ATG GTG CTG ACG GGT ACC CAT CTA GCT TGG       145
Arg Leu Pro Ile Val Pro Met Val Leu Thr Gly Thr His Leu Ala Trp

AGG AAG AAC AGT TTG CGA GTC AGA CCA GCA CCT ATC ACA GTG AAA           190
Arg Lys Asn Ser Leu Arg Val Arg Pro Ala Pro Ile Thr Val Lys

TAC TTC TCA CCC ATA AAA ACT GAT GAC TGG GAA GAA GAA AAG ATC           235
Tyr Phe Ser Pro Ile Lys Thr Asp Asp Trp Glu Glu Glu Lys Ile

AAT CAT TAT GTG GAA ATG ATC CAC ATGATGATGA TG                         271
Asn His Tyr Val Glu Met Ile His (2) INFORMATION FOR SEQ ID NO: 19:

(i) SEQUENCE CHARACTERISTICS:
        (A) LENGTH:  358 base pairs
        (B) TYPE:   nucleic acid
        (C) STRANDEDNESS:  single
        (D) TOPOLOGY:    linear (ii) MOLECULE TYPE:   cDNA to mRNA (xi) SEQUENCE DESCRIPTION: SEQ ID NO: 19:

CTACTACTAC TA ATA ATA TTC CCC GAA GGT ACT CGA TCG AAA ACA GGA AGG      51
            Ile Ile Phe Pro Glu Gly Thr Arg Ser Lys Thr Gly Arg

CTG CTT CCA TTT AAG AAG GTAACGATCA TAACATGCGT GTATATTTGT               99
Leu Leu Pro Phe Lys Lys

ATGTTTATCC ATTTTATTCT TCTGCTTGTG CTTCTCGTTT CTTCATTTTC TGTTGCAG       157
```

```
GGT TTT ATT CAC ATA GCA CCT CAG ACA CGG TTG CCG ATA GTT CCA ATG        205
Gly Phe Ile His Ile Ala Pro Gln Thr Arg Leu Pro Ile Val Pro Met

GTG CTG ACG GGT ACC CAT CTA GCT TGG AGG AAG AAC AGT TTG CGA GTC        253
Val Leu Thr Gly Thr His Leu Ala Trp Arg Lys Asn Ser Leu Arg Val

AGA CCA GCA CCT ATC ACA GTG AAA  TAC TTC TCA CCC ATA AAA ACT GAT       301
Arg Pro Ala Pro Ile Thr Val Lys  Tyr Phe Ser Pro Ile Lys Thr Asp

GAC TGG GAA GAA GAA AAG ATC AAT CAT TAT GTC GAA ATG ATT CAC            346
Asp Trp Glu Glu Glu Lys Ile Asn His Tyr Val Glu Met Ile His

ATGATGATGA TG                                                          358

(2) INFORMATION FOR SEQ ID NO: 20:

(i) SEQUENCE CHARACTERISTICS:
        (A) LENGTH:   218 base pairs
        (B) TYPE:    nucleic acid
        (C) STRANDEDNESS:  single
        (D) TOPOLOGY:    linear (ii) MOLECULE TYPE:   cDNA to mRNA (xi) SEQUENCE DESCRIPTION: SEQ ID NO: 20:

TACTACTACT A ATA ATA TTT CCC GAG GGT ACT CGA TCG AAA ACA GGA AGG        50
             Ile Ile Phe Pro Glu Gly Thr Arg Ser Lys Thr Gly Arg

CTG CTT CCA TTT AAG AAG GGT TTT ATT CAC ATA GCA CTT CAG ACA CGG         98
Leu Leu Pro Phe Lys Lys Gly Phe Ile His Ile Ala Leu Gln Thr Arg

TTG CCG ATA GTT CCA ATG GTG CTG ACG GGT ACC CAT CTA GCT TGG AGG        146
Leu Pro Ile Val Pro Met Val Leu Thr Gly Thr His Leu Ala Trp Arg

AAG AAC AGT TTG CGA GTC AGA CCA GCA CCT ATC ACA GTG AAA  TAC TTT       194
Lys Asn Ser Leu Arg Val Arg Pro Ala Pro Ile Thr Val Lys  Tyr Phe

TCG CCG ATC AAA ATGATGATGA TG                                          218
Ser Pro Ile Lys
```